United States Patent
Hsing et al.

(10) Patent No.: US 11,965,204 B2
(45) Date of Patent: Apr. 23, 2024

(54) DETECTION OF ANALYTES BY ENZYME-MEDIATED STRAND DISPLACEMENT REACTIONS

(71) Applicant: The Hong Kong University of Science and Technology, Hong Kong (CN)

(72) Inventors: I-Ming Hsing, Hong Kong (CN); Alan Fernando Rodriguez Serrano, Hong Kong (CN)

(73) Assignee: The Hong Kong University of Science and Technology, Hong Kong (CN)

(*) Notice: Subject to any disclaimer, the term of this patent is extended or adjusted under 35 U.S.C. 154(b) by 179 days.

(21) Appl. No.: 17/444,038

(22) Filed: Jul. 29, 2021

(65) Prior Publication Data

US 2022/0042081 A1   Feb. 10, 2022

Related U.S. Application Data

(60) Provisional application No. 63/103,492, filed on Aug. 6, 2020.

(51) Int. Cl.
| | | |
|---|---|---|
| C07H 21/04 | (2006.01) | |
| C12N 15/113 | (2010.01) | |
| C12Q 1/6816 | (2018.01) | |

(52) U.S. Cl.
CPC .......... *C12Q 1/6816* (2013.01); *C12N 15/113* (2013.01); *C12N 2310/16* (2013.01)

(58) Field of Classification Search
None
See application file for complete search history.

(56) References Cited

U.S. PATENT DOCUMENTS 8,652,804 B2   2/2014   Dietrich et al.

FOREIGN PATENT DOCUMENTS

| CN | 110283887 A | 9/2019 |
|---|---|---|
| WO | WO-2019/113075 A2 | 6/2019 |
| WO | WO-2020/097610 A1 | 5/2020 |
| WO | WO-2020/207453 A1 | 10/2020 |

OTHER PUBLICATIONS

Libis et al. Current Opinion in Microbiology 2016, 33: 105-112.*
Liang, M. et al., "A CRISPR-Cas12a-derived biosensing platform for the highly sensitive detection of diverse small molecules," *Nature Communications*, 2019, 10:1-9.
Yao, Y. et al., "A novel signal transduction system for development of uric acid biosensors," *Applied Microbiology and Biotechnology*, Jun. 30, 2018, 102:7489-7497, Springer-Verlag GmbH.
Jung, J. K. et al., "Cell-free biosensors for rapid detection of water contaminants," *Nature Biotechnology*, Dec. 2020, 38:1451-1459.
Yao, Y. et al., "Development of small molecule biosensors by coupling the recognition of the bacterial allosteric transcription factor with isothermal strand displacement amplification," *Chem. Commun.*, 2018, 54:4774-4777, The Royal Society of Chemistry.
Cao, J. et al., "Harnessing a previously unidentified capability of bacterial allosteric transcription factors for sensing diverse small molecules in vitro," *Science Advances*, Nov. 28, 2018, pp. 1-11.
Bollella, P. et al., "Control of Allosteric Protein Electrochemical Switches with Biomolecular and Electronic Signals," *The Journal of Physical Chemistry Letters*, Jun. 17, 2020, 11:5549-5554, American Chemical Society.
Lu, S. et al., "Small Molecule Allosteric Modulators of G-Protein-Coupled Receptors: Drug-Target Interactions," *Journal of Medicinal Chemistry*, 2019, 62:24-45, American Chemical Society.
Gowal, R. et al., "Antibiotic Pollution in the Environment: A Review," *CLEAN Soil Air Water*, 2015, 43(4):479-489, Wiley-VH Verlag GmbH & Co. KGaA.
Nguyen, T. T. et al., "A Förster Resonance Energy Transfer-Based Ratiometric Sensor with the Allosteric Transcription Factor TetR," *Small*, 2020, pp. 1-18, Wiley-VCH Verlag GmbH & Co. KGaA.
Michelini, E. et al., "Field-deployable whole-cell bioluminescent biosensors: so near and yet so far," *Anal Bioanal Chem.*, 2013, 405:6155-6163, Springer-Verlag.
Rosso, J. J. et al., "Concentration of arsenic in water, sediments and fish species from naturally contaminated rivers," *Environ Geochem Health*, 2013, 35:201-214, Springer Science+Business Media B.V.
Tang, W. et al., "DNA Strand Displacement Reaction: A Powerful Tool for Discriminating Single Nucleotide Variants," *Topics in Current Chemistry*, 2020, 378(10):1-30, Springer Nature Switzerland AG.
Ravikumar, A. et al., "MoS$_2$ nanosheets as an effective fluorescent quencher for successive detection of arsenic ions in aqueous system," *Applied Surface Science*, 2018, 449:31-38, Elsevier B.V.
Ma, Z. et al., "Whole-cell paper strip biosensors to semi-quantify tetracycline antibiotics in environmental matrices," *Biosensors and Bioelectronics*, 2020, 168:1-31, Elsevier B.V.
Rosen, R., "Mass spectrometry for monitoring micropollutants in water," *Current Opinion in Biotechnology*, 2007, 18:246-251, Elsevier Ltd.
Pan, J. et al., "Ultrasensitive aptamer biosensor for arsenic (III) detection based on label-free triple-helix molecular switch and fluorescence sensing platform," *Talanta*, 2018, 189:370-376, Elsevier B.V.
Gan, Y. et al., "In-situ detection of cadmium with aptamer functionalized gold nanoparticles based on smartphone-based colorimetric system," *Talanta*, 2020, 208:1-7, Elsevier B.V.

(Continued)

*Primary Examiner* — Kimberly Chong
(74) *Attorney, Agent, or Firm* — SALIWANCHIK, LLOYD & EISENSCHENK

(57) ABSTRACT

The subject invention pertains to composition and methods of using said composition as an in vitro biosensor of small molecules in biological and/or environmental samples using enzyme-assisted nucleic acid reactions. The methods and compositions can be used to sense and/or transduce the signal of a sensing event mediated by allosteric proteins, endonucleases and nucleic acid reactions. This invention allows the rapid development and setup of one-pot assays to provide results in minutes. The methods and compositions may be used to generate an electrochemical, fluorescent, colorimetric, and/or luminescent output and the methods can be performed in different modalities, including a solution-based or paper-based assay.

9 Claims, 15 Drawing Sheets

Specification includes a Sequence Listing.

(56) References Cited

OTHER PUBLICATIONS

Song, S. et al., "Aptamer-based biosensors," *Trends in Analytical Chemistry*, 2008, 27(2):108-117, Elsevier Ltd.
Zhang, Z. et al., "Nucleic Acid Self-Assembly Circuitry Aided by Exonuclease III for Discrimination of Single Nucleotide Variants," *Analytical Chemistry*, 2017, 89:12466-12471, American Chemical Society.
Vanarsdale, E. et al., "Redox-Based Synthetic Biology Enables Electrochemical Detection of the Herbicides Dicamba and Roundup via Rewired *Escherichia coli*," *ACS Sensors*, 2019, 4:1-16, American Chemical Society.
Wen, K. Y. et al., "A Cell-Free Biosensor for Detecting Quorom Sensing Molecules in *P. aeruginosa*—Infected Respiratory Samples," *ACS SyntheticBiology*, 2017, 6:1-26, American Chemical Society.
Silverman, A. D. et al., "Design and Optimization of a Cell-Free Atrazine Biosensor," *ACS SyntheticBiology*, 2020, 9:1-14, American Chemical Society.
Zhang, D. Y. et al., "Control of DNA Strand Displacement Kinetics Using Toehold Exchange," *J. Am. Chem. Soc.*, 2009, 131:1-28, American Chemical Society.
Yurke, B. et al., "Using DNA to Power Nanostructures," *Genetic Programming and Evolvable Machines*, 2003, 4:111-122, Kluwer Academic Publishers.
Machinek, R. R. F. et al., "Programmable energy landscapes for kinetic control of DNA strand displacement," *Nature Communications*, Nov. 10, 2014, 5:1-46, Macmillan Publishers Limited.
Chen, Y. et al., "A DNA logic gate based on strand displacement reaction and rolling circle amplification, responding to multiple low-abundance DNA fragment input signals, and its application in detecting miRNAs," *Chem. Commun.*, 2015, 51:1-9, The Royal Society of Chemistry.
Zhang, Z. et al., "Integrating DNA strand displacement circuitry to the nonlinear hybridization chain reaction," *Nanoscale*, 2017, 9:1-16, The Royal Society of Chemistry.
Iwasaki, R. S. et al., "SPRINT: a Cas13a-based platform for detection of small molecules," *Nucleic Acid Research*, 2020, 48(17):1-31.
Gavilán, R. E. et al., "A Confirmatory Method Based on HPLC-MS/MS for the Detection and Quantification of Residue of Tetracyclines in Nonmedicated Feed," *Journal of Analytical Methods in Chemistry*, 2016, pp. 1-9.
Damania, R. et al., "Quality Unknown the Invisible Water Crisis," 2019, pp. 1-142, International Bank for Reconstruction and Development.
Fernandez-López, R. et al., "Transcription factor-based biosensors enlightened by the analyte," *Frontiers in Microbiology*, Jul. 1, 2015, 6(648):1-21.
Dada, E. O. et al., "Phthalate and Metal Concentrations in Drinking Water in Lagos, Nigeria," *Journal of Health & Pollution*, Jun. 2018, 8(18):1-8.
Grazon, C. et al., "A progesterone biosensor derived from microbial screening," *Nature Communications*, 2020, 11:1-40.
Rodríguez-Serrano, A. et al., "Allosteric Regulation of DNA Circuits Enables Minimal and Rapid Biosensors of Small Molecules," *ACS SyntheticBiology*, 2021, 10:1-25.

\* cited by examiner

DETECTION OF ANALYTES BY ENZYME-MEDIATED STRAND DISPLACEMENT REACTIONS

CROSS-REFERENCE TO RELATED APPLICATION

This application claims the benefit of U.S. Provisional Application Ser. No. 63/103,492, filed Aug. 6, 2020, which is hereby incorporated by reference in its entirety including any tables, figures, or drawings.

The Sequence Listing for this application is labeled "SeqList.txt" which was created on May 11, 2021 and is 10 KB. The entire content of the sequence listing is incorporated herein by reference in its entirety.

FIELD OF THE INVENTION

The present invention generally relates to in vitro detection of small molecules. Particularly, the invention relates to allosteric proteins, endonucleases and nucleic acid compositions and methods of use for the detection of small molecules or metabolites.

BACKGROUND OF THE INVENTION

Biosensors for small molecules rely on the combination of recognition and signal transduction elements. Generally, the small molecule-sensitive recognition biomolecules used in biosensors are aptamers, antibodies, and allosteric Transcription Factors (aTFs)[1]. aTFs are proteins that bind to DNA and effector molecules via different domains, and the binding of the effector significantly affects the affinity for the DNA. This allostery of many natural and engineered transcription factors has been leveraged to develop in vivo and in vitro biosensors of cognate ligands.[2-5]

Allosteric Transcription Factors in in vitro biosensors can be generally found in: 1) cell-free systems, where they modulate the activity of RNA polymerases on their promoters[6,7] and 2) platforms that couple the responsive protein with molecular signal transduction strategies. At present, many methods exploit the competition of an aTF with another DNA-interacting biomolecule, generally enzymes, for the same double stranded DNA fragment. Overall, when the cognate ligand is present and the aTF-ligand complex dissociates from the DNA, the competing enzyme can act on the DNA and generate a product that can be amplified later. For example, T4 ligase can be used to compete with an aTF for a nicked double stranded DNA substrate, with the nick in the binding sequence of the aTF. After the aTF responds to the effector, T4 ligase can repair the DNA and it can be amplified by polymerase chain reaction (PCR), recombinase polymerase amplification (RPA), or rolling circle amplification (RCA).[8] Competition of the aTF HosA with the Klenow Fragment (KF) has been used to detect p-hydroxybenzoic acid (PHBA). When PHBA is present, the KF along with Nb.BbvCI (a nicking endonuclease) start cycles of strand displacement amplification (SDA), in which the products of SDA fold into G-quadruplexes and are probed to generate a fluorescent or colorimetric signals.[9] The restriction endonuclease HindIII has also been used to cleave the DNA binding sequence of HucR in the presence of uric acid, resulting in a negative correlation between the uric acid concentration and Ct-value of qPCR.[10] Recently, a platform based on Cas12a was developed to detect uric acid.[11] The formation of the aTF-ligand complex allows the Ribonucleoprotein (RNP) to bind and cleave the target DNA, thus activating the trans-cleavage activity of Cas12a for the generation of a fluorescent signal.

At present, the methods developed face many drawbacks. Most require several preparation steps, which may include many incubation steps, equilibrations, washes, and centrifugation. This impacts the total time from reaction preparation to results and increases the complexity of the test. As well, one-pot assays are not feasible given the separation of the sensing and amplification steps. Additionally, platforms that require modification and/or immobilization of aTFs are less flexible, as these are techniques that may have variable processing and efficiency depending on the aTF. As well, many biosensors suffer from long turnaround time (>100 min), complex formulation and chemical modifications, low sensitivity, or high variability. Finally, most of the techniques rely on nucleic acid amplification techniques, which increase the cost and complexity of the test.

Therefore, there remains a need for a platform to detect small molecules quickly and accurately without many of the noted drawbacks.

BRIEF SUMMARY OF THE INVENTION

The present invention pertains to compositions and methods of an in vitro biosensor of small molecules in biological and/or environmental samples using enzyme-assisted nucleic acid reactions. The compositions and methods can be used to sense and/or transduce the signal of a sensing event mediated by allosteric proteins or aptamers, endonucleases, and nucleic acid reactions. The compositions and methods may be used to generate an electrochemical, fluorescent, colorimetric, and/or luminescent output and the methods can be performed in different modalities, such as solution-based, paper-based, and with microfluidic devices. The methods, components and compositions can be modified to different preservation techniques, such as, for example, lyophilization and on-paper drying.

The methods comprise the molecular mechanisms, experimental set-up, reactions components and compositions, and signal generation and measurement. In general, the test samples can be prepared and treated prior to the detection. The preparation may include filtration, centrifugation, changes in temperature, solubilization, dilution or concentration of the target molecule in the test sample. The molecular mechanism and experimental set-up allow the sensing of specific target small molecules/metabolites in the test samples mediated by allosteric proteins or aptamers. If the target small molecule/metabolite is present in the test sample, it can bind to the allosteric protein or aptamer and trigger cycles of Toehold-mediated Strand Displacement reactions enabled by an endonuclease. The accumulating final displaced product can be probed by electrochemical, fluorescent, colorimetric, and/or luminescent methods. Toehold-mediated Strand Displacement amplification allows for the integration of biosensing and signal transduction in a one-pot assay, making the method simple and fast, due to the use of the competing enzyme or structural change or a DNA template in cycles of signal amplification process without the need of nucleic acid amplification (synthesis), which is used in existing methods. This approach can be applied to virtually any allosteric protein/ligand complex or aptamer, in which the allosteric protein or aptamer can work as repressor or activator.

The experimental set-up and reactions may include variations in the modality of the biosensing strategy. Components and compositions may be adapted to immobilization-based reactions.

BRIEF DESCRIPTION OF THE DRAWINGS

FIG. 5A shows Electrophoretic mobility shift assay (EMSA) for confirmation of TetR binding to the DNA template (S) containing HgaI Recognition Site and tetO sequence; and unbinding in presence of tetracycline (Tc). FIG. 5B PAGE showing the effect of 2-bp spacers (N=0-12) on HgaI cleavage of DNA protected by TetR. 50 nM of DNA were incubated with 250 nM of TetR and 1 U of HgaI for 30 minutes at 37° C. Immediately after, the proteins were digested with 0.4 U of Proteinase K for 15 minutes at 37° C. The rectangle indicates the cleavage products of S. The arrow indicates TetR/S complex due to incomplete digestion of TetR by Proteinase K. FIG. 5C EMSA showing the regulation of HgaI cleavage by Tc. Increasing concentrations of Tc result in higher amount of cleaved products.

FIG. 6A shows environmental samples taken at a pond in Hong Kong. After collection, samples were spiked with different antibiotics (where applicable) and immediately filtered using a syringe-filter. FIG. 6B shows the overall workflow from sample filtration to result can be accomplished within 25 minutes. FIG. 6C shows that the sensors successfully reported the presence of spiked-in antibiotics in water samples with no crosstalk. 500 nM of each ligand were used for the TetR-based biosensors (250 nM final concentration). 2.5 µM of each ligand were used for the MphR-based biosensors (1.25 µM final concentration). (ns: p-value >0.05 between non-cognate ligand and WS using a two-tailed t-test). Tc=Tetracycline, Ery=Erythromycin, Amp=Ampicillin, Kan=Kanamycin, WS=Water Sample (no analyte). Bars indicate mean values and error bars indicate s.d. n=2 (FIG. 6C).

FIG. 7A illustrates the components of the biosensor, indicating the DNA template (S) and Invading Probe (IP) sequences and modifications. FIG. 7B demonstrates the repression of the reaction using different concentrations of TetR (0 nM, 50 nM, 10 nM 0, 150 nM, and 200 nM).

FIG. 9A illustrates the components of the biosensor, indicating the DNA template (S) and Invading Probe (IP) sequences and modifications. FIG. 9B demonstrates the repression of the reaction using different concentrations of MphR (0 nM, 750 nM, 1.5 uM, 2.25 uM, and 3 uM).

FIG. 11A shows the structural change in the DNA template S upon hybridization with the Invading Probe (IP) after target-induced dissociation of the aptamer. Similarly, FIG. 11B shows the structural change of an aptamer switch composed of an aptamer region and an S regions. After the structural change, both mechanisms can enter the signal amplification circuit.

FIG. 12A shows the structure and minimum free energy (MFE) of two different hairpins (SH and LH) from S. FIG. 12B shows that the length of the hairpin's stem has an effect on the rate and leakage of the signal amplification circuit, and the final concentration of cleaved fluorescent product. SH and LH are systems without aptamer, while SH Repressed and LH Repressed are systems with an equimolar concentration of aptamer over S. In all cases: the reaction volume is 10 uL, in which the concentration of HgaI, S, and IP are 100 U/mL, 50 nM, and 1.25 uM, respectively.

BRIEF DESCRIPTION OF THE SEQUENCES

Figure 1:
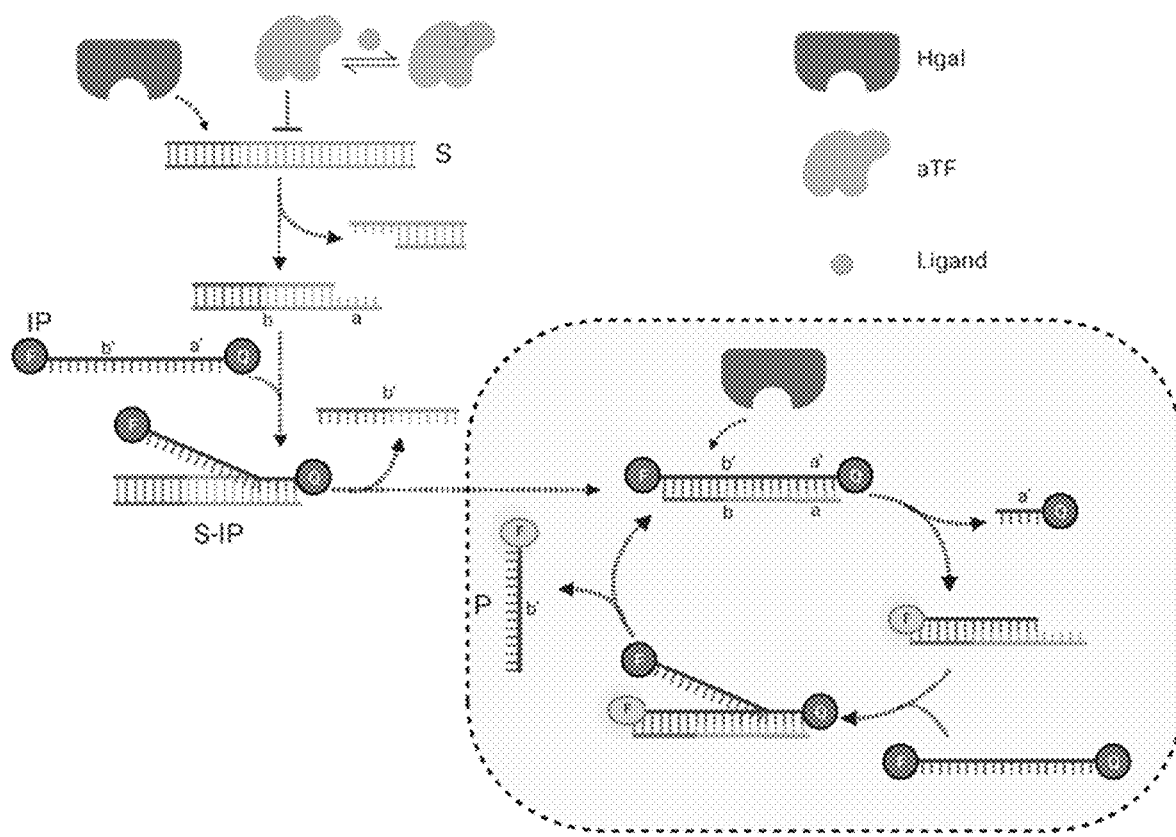
FIG. 1 is an illustration of the in vitro biosensor of small molecules/metabolites. A natural or engineered allosteric protein (aTF) binds to a double stranded DNA fragment that contains its cognate DNA-binding sequence. The binding of this protein hinders the cleavage of the DNA-binding sequence by a restriction endonuclease Type IIS (HgaI in this example) which recognition site is either upstream or downstream of the DNA-binding sequence. Its cleavage site is located in the allosteric protein binding sequence. The presence of the allosteric protein's cognate effector or ligand, e.g. small molecule or metabolite, causes its dissociation from the binding DNA sequence, which allows HgaI to bind to its recognition site and cleave the allosteric protein binding DNA sequence. This cleavage generates a 5' overhang (short portion of single stranded DNA) of five nucleotides in length. This overhang serves as a toehold domain and nucleation site for an invading probe (IP), which initiates a Toehold-mediated Strand Displacement reaction. The IP is labelled with a fluorophore and a quencher at the 5' and 3' ends, respectively. The result of this reaction is an intermediary (S-IP) that can be cleaved by the HgaI protein but lacks the full binding sequence for the allosteric protein. The cleavage generates a toehold domain that starts another Toehold-mediated Strand Displacement reaction and results in the displacement of a fragment of the IP (P), which generates a fluorescent signal. The new S-IP enters a cycling reaction of cleavage by the Restriction Enzyme Type IIS and Toehold-mediated Strand Displacement events. Throughout the cycles, the total amount of IP decreases and P increases. Each cycle results in the accumulation of the displaced fluorescent product (P), which fluorescent signal can be measured across time or endpoint.

SEQ ID NO: 1 E. coli nucleotide sequence encoding TetR
SEQ ID NO: 2: Exemplary DNA template sequence for use with TetR sensor molecule
SEQ ID NO: 3: Complementary sequence of SEQ ID NO: 2
SEQ ID NO: 4: Exemplary invading probe
SEQ ID NO: 5: Exemplary DNA template sequence for use with TetR sensor molecule
SEQ ID NO: 6: Complementary sequence of SEQ ID NO: 5
SEQ ID NO: 7: Exemplary DNA template sequence for use with TetR sensor molecule
SEQ ID NO: 8: Complementary sequence of SEQ ID NO: 7
SEQ ID NO: 9: Exemplary DNA template sequence for use with TetR sensor molecule
SEQ ID NO: 10: Complementary sequence of SEQ ID NO: 9
SEQ ID NO: 11: Exemplary DNA template sequence for use with TetR sensor molecule
SEQ ID NO: 12: Complementary sequence of SEQ ID NO: 11
SEQ ID NO: 13: Exemplary DNA template sequence for use with TetR sensor molecule
SEQ ID NO: 14: Complementary sequence of SEQ ID NO: 13
SEQ ID NO: 15: Exemplary DNA template sequence for use with TetR sensor molecule
SEQ ID NO: 16: Complementary sequence of SEQ ID NO: 15
SEQ ID NO: 17: Exemplary DNA template sequence for use with MphR sensor molecule
SEQ ID NO: 18: Complementary sequence of SEQ ID NO: 17
SEQ ID NO: 19: Exemplary invading probe
SEQ ID NO: 20: Exemplary invading probe
SEQ ID NO: 21 E. coli amino acid sequence of TetR
SEQ ID NO: 22 E. coli amino acid sequence of MphR

DETAILED DISCLOSURE OF THE INVENTION

Selected Definitions

As used herein, the singular forms "a," "an," and "the" are intended to include the plural forms as well, unless the context clearly indicates otherwise. Further, to the extent that the terms "including," "includes," "having," "has," "with," or variants thereof are used in either the detailed description and/or the claims, such terms are intended to be inclusive in a manner similar to the term "comprising." The transitional terms/phrases (and any grammatical variations thereof) "comprising," "comprises," "comprise," include the phrases "consisting essentially of," "consists essentially of" "consisting," and "consists."

The phrases "consisting essentially of" or "consists essentially of" indicate that the claim encompasses embodiments containing the specified materials or steps and those that do not materially affect the basic and novel characteristic(s) of the claim.

The term "about" means within an acceptable error range for the particular value as determined by one of ordinary skill in the art, which will depend in part on how the value is measured or determined, i.e., the limitations of the measurement system. Where particular values are described in the application and claims, unless otherwise stated the term "about" meaning within an acceptable error range for the particular value should be assumed.

In the present disclosure, ranges are stated in shorthand, to avoid having to set out at length and describe each and every value within the range. Any appropriate value within the range can be selected, where appropriate, as the upper value, lower value, or the terminus of the range. For example, a range of 1-10 represents the terminal values of 1 and 10, as well as the intermediate values of 2, 3, 4, 5, 6, 7, 8, 9, and all intermediate ranges encompassed within 1-10, such as 2-5, 2-8, and 7-10. Also, when ranges are used herein, combinations and sub-combinations of ranges (e.g., subranges within the disclosed range) and specific embodiments therein are intended to be explicitly included.

As used herein and in the claims, a "sample" refers to a sample of cell, tissue, solid, or fluid, including but not limited to, for example, skin, plasma, serum, spinal fluid, lymph fluid, synovial fluid, urine, tears, blood cells, organs, tumors, environmental sources, including waterways, soil, or air, samples of in vitro cell culture constituents (including but not limited to conditioned medium resulting from the growth of cells in cell culture medium, recombinant cells and cell components), or any other source derived from an organism or containing an organism.

The term "organism" as used herein includes viruses, bacteria, fungi, plants and animals. Additional examples of organisms are known to a person of ordinary skill in the art and such embodiments are within the purview of the materials and methods disclosed herein. The assays described herein can be useful in analyzing any genetic material obtained from any organism.

A "template" or "template sequence" as used herein is a polynucleotide (e.g., as defined herein, including a DNA, RNA, or DNA/RNA hybrid, as well as modified forms thereof) that includes a "target site." The terms "target site" is used to refer to a nucleic acid sequence present in a template sequence to which a probe (e.g., any herein), protein, or other nucleotide sequence will bind provided sufficient conditions (e.g., sufficient complementarity) for binding exist. Suitable DNA/RNA binding conditions include physiological conditions normally present in a cell. Other suitable binding conditions (e.g., conditions in a cell-free system) are known in the art.

The term "hybridizes with" when used with respect to two sequences indicates that the two sequences are sufficiently complementary to each other to allow nucleotide base pairing between the two sequences. Sequences that hybridize with each other can be perfectly complementary but can also have mismatches to a certain extent. Therefore, the sequences of the probes or other hybridizing sequences may have a few mismatches with the corresponding target sequences but will still function as intended as long as the probes or other hybridizing sequences can hybridize with the target sequences. Depending upon the stringency of hybridization, a mismatch of up to about 5% to 20% between the two complementary sequences would allow for hybridization between the two sequences. Typically, high stringency conditions have higher temperature and lower salt concentration and low stringency conditions have lower temperature and higher salt concentration. High stringency conditions for hybridization are preferred. With respect to two sequences indicates that the two sequences are sufficiently complementary to each other to allow nucleotide base pairing between the two sequences.

"Hybridizing conditions" refer to conditions of temperature, pH, and concentrations of reactants that allow at least a portion of complementary sequences to anneal with each other. Conditions required to accomplish hybridization depend on the size of the oligonucleotides to be hybridized, the degree of complementarity between the oligonucleotides, and the presence of other materials in the hybridization reaction admixture. The actual conditions necessary for each hybridization step are well known in the art or can be readily determined by a person of ordinary skill in the art. Typical hybridizing conditions include the use of solutions buffered to a pH from about 7 to about 8.5 and temperatures of from about 30° C. to about 80° C.; preferred conditions comprise using Tris-EDTA buffer at pH 7.5 and $MgCl_2$ at about 5 mM to about 15 mM. The mixed oligos are heated to 95° C. and slowly cooled down to 20° C. over 180 min. In certain embodiments, the temperature of the hybridization must be lower than the melting temperature of the DNA duplex. Hybridization conditions may also include a buffer that is compatible, i.e., chemically inert, with respect to the oligonucleotides and other components, yet still allows for hybridization between complementary base pairs.

As used herein, the phrases "operably linked" or "operatively linked" or "operatively associated with," as used interchangeably, refers to a juxtaposition wherein the components so described are in a relationship permitting them to function in their intended manner. A first component can be operably linked to a second component by way of any useful bond (e.g., a covalent bond, a non-covalent bond, and/or linked via van der Waals forces, hydrogen bonds, and/or other intermolecular forces, such as those including a π-π interaction, a salt bridge, or a cation-it interaction) or any useful linker (e.g., nucleotide sequence or any herein).

Throughout this disclosure, different sequences are described by specific nomenclature, for example, target sequence and probe sequence. When such nomenclature is used, it is understood that the identified sequence is substantially identical or substantially reverse complementary to at least a part of the corresponding sequence. For example, "an invading probe sequence" describes a sequence that is substantially identical to at least a part of the invading probe sequence or substantially reverse complementary to at least a part of the invading probe sequence. Thus, the nomenclature is used herein to simplify the description of different polynucleotides and parts of polynucleotides used in the methods disclosed here; however, a person of ordinary skill in the art would recognize that appropriate substantially identical or substantially reverse complementary sequences to at least a part of the corresponding sequences could be used to practice the methods disclosed herein.

Also, two sequences that correspond to each other, for example, a probe binding sequence a DNA template sequence, or an aptamer sequence, have at least 90% sequence identity, preferably, at least 95% sequence identity, even more preferably, at least 97% sequence identify, and most preferably, at least 99% sequence identity, over at least 70%, preferably, at least 80%, even more preferably, at least 90%, and most preferably, at least 95% of the sequences. Alternatively, two sequences that correspond to each other are reverse complementary to each other and have at least 90% perfect matches, preferably, at least 95% perfect matches, even more preferably, at least 97% perfect matches, and most preferably, at least 99% perfect matches in the reverse complementary sequences, over at least 70%, preferably, at least 80%, even more preferably, at least 90%, and most preferably, at least 95% of the sequences. Thus, two sequences that correspond to each other can hybridize with each other or hybridize with a common reference sequence over at least 70%, preferably, at least 80%, even more preferably, at least 90%, and most preferably, at least 95% of the sequences. Preferably, two sequences that correspond to each other are 100% identical over the entire length of the two sequences or 100% reverse complementary over the entire length of the two sequences.

As used herein, the phrase "allosteric proteins" refer to proteins that directly couple the recognition of a molecule of interest to a response. Allostery is a common feature of proteins, in which the behavior at an 'active' site is altered by binding of an effector to a second or 'allosteric' site, often quite distant from the first. The altered behavior can either directly or indirectly lead to a change in the protein's activity and thereby elicit a detectable response.

As used herein, the term "toehold" refers to nucleation site of a domain comprising a nucleic acid sequence designed to initiate hybridization of the domain with a complementary nucleic acid sequence. The secondary structure of a nucleic acid sequence may be such that the toehold is exposed or sequestered. For example, in some embodiments, the secondary structure of the toehold is such that the toehold is available to hybridize to a complementary nucleic acid (the toehold is "exposed," or "accessible"), and in other embodiments, the secondary structure of the toehold is such that the toehold is not available to hybridize to a complementary nucleic acid (the toehold is "sequestered," or "inaccessible"). If the toehold is sequestered or otherwise unavailable, the toehold can be made available by some event such as, for example, the opening of the hairpin of which it is a part of or cleavage of a sequence by a restriction enzyme. When exposed, a toehold is configured such that a complementary nucleic acid sequence can nucleate at the toehold.

As used herein, an "aptamer" is an oligonucleotide that is able to specifically bind an analyte of interest other than by base pair hybridization. Aptamers typically comprise DNA or RNA or a mixture of DNA and RNA but can also comprise protein, either in addition to nucleotides or without nucleotides. Aptamers may be naturally occurring or made by synthetic or recombinant means. The aptamers are typically single stranded, but may also be double stranded or triple stranded. They may comprise naturally occurring nucleotides, nucleotides that have been modified in some way, such as by chemical modification, and unnatural bases. The aptamers may be chemically modified, for example, by the addition of a label, such as a fluorophore, or by the addition of a molecule that allows the aptamer to be cross-linked to a molecule to which it is bound. Aptamers are of the same "type" if they have the same sequence or are capable of specific binding to the same molecule. The length of the aptamer will vary, but is typically less than about 100 nucleotides.

As used herein, the term "cleavage" refers to the breakage of the covalent backbone of a nucleic acid molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends.

As used herein, the terms "nuclease" and "endonuclease" and the phrase "restriction enzyme" are used interchangeably herein to mean an enzyme which possesses catalytic activity for DNA cleavage.

A substance is commonly said to be present in "excess" or "molar excess" relative to another component if that component is present at a higher molar concentration than the other component. Often, when present in excess, the component will be present in at least about a 2-fold, at least about a 5-fold mold, or at least about a 10-fold molar excess and commonly at 100-1,000,000 fold molar excess. Those of skill in the art would appreciate and understand the particular degree or amount of excess preferred for any particular reaction or reaction conditions. Such excess is often empirically determined and/or optimized for a particular reaction or reaction conditions.

The disclosure provides material and methods that solve the problems associated with conventional methods for detecting small molecules, while expediting the process.

Certain embodiments of the present invention refer to a method for determining the presence of an analyte in a sample comprising the a) contacting an endonuclease, DNA template, sensor molecule, and an invading probe with the sample, wherein the sensor molecule can inhibit the recognition of a restriction site in the DNA template by the restriction enzyme; b) binding or hybridizing the sensor molecule to the DNA template, wherein the sensor molecule excludes the restriction enzyme from a restriction site specific to said restriction enzyme in the DNA template in the absence of the analyte or displacing the sensor molecule from the DNA template when the analyte binds to the sensor molecule; c) optionally, digesting the DNA template with the restriction enzyme; d) optionally, hybridizing the invading probe to the DNA template; e) optionally, cleaving the hybridized invading probe and DNA template with the restriction enzyme; and f) determining the presence or absence of at least one analyte by detecting a signal emitted from the invading probe, wherein detection of said signal is indicative of the presence of the analyte. Certain embodiments also provide compositions for analyte detection comprising a restriction enzyme, a DNA template, a sensor molecule, and an invading probe, wherein the analyte binds to the sensor molecule and permits recognition of a restriction site in the DNA template by the restriction enzyme. In certain embodiments, the invading probe generates a detectable signal in conjunction with a reporter molecule using Toehold-mediate strand displacement. In certain embodiments, the sample can be treated prior to the contact to the reaction mixture by heating, centrifugation, chemical or physical solubilization, dilution, concentration, or filtration.

DNA Template and Toehold-Mediated Strand Displacement

The present methods allow for the detection a wide variety of target molecules. In one aspect, the present invention relates to compositions and methods for using a sensor molecule, such as, for example, an allosteric protein, a transcription factor, aptamer, or aptasensor, which binds to and allows detection of a target molecule, wherein the sensor inhibits an endonuclease from binding and cleaving the DNA template.

In certain embodiments, the DNA template can be single or double-stranded. In certain embodiments, the DNA template can have at least one, two, three, four, five, six, seven, eight or more sequences that facilitate processing or detection of an analyte. Such sequences include restriction or endonuclease sites, particularly Type IIS endonuclease sites, spacer sequences that range from about 1 to about 20 base pairs, and/or at least one, two, three, four, five, six, seven, eight or more sites that are complementary to an aptamer. In certain embodiments, the DNA template can have an operator sequence, which is preferably the DNA binding sequence of the sensor molecule. In certain embodiments, the sequences, including the operator sequences, restriction sites and the sequences complementary to an aptamer, are operably linked. In certain embodiments in which two or more sites that facilitate processing or detection of an analyte are present (e.g., restriction site, operator sequence, or aptamer commentary region), the sites can be separated zero base pairs or by at least 1, 2, 3, 4, 5, 6, 7, 8, 9, 10, 11, 12, 13, 14, 15, 16, 17, 18, 19, 20, 25, 30, 35, 40, 35, 50, 75, 100, or more base pairs. In preferred embodiments in which two or more sites that facilitate processing or detection of an analyte are present (e.g., restriction site, operator sequence, or aptamer commentary region), the sites can be separated about 4 to about 15 base pairs.

In certain embodiments, the binding and cleavage by a restriction enzyme to the DNA template can permit a probe to hybridize to the cleaved DNA template and initiate Toehold-mediated Strand Displacement, a process well-known in the art as described in U.S. Pat. No. 9,284,602 and Simmel F C, Yurke B, Singh H R. Principles and Applications of Nucleic Acid Strand Displacement Reactions. Chem Rev. 2019 May 22; 119(10):6326-6369. doi: 10.1021/acs.chemrev.8b00580. Epub 2019 Feb. 4. PMID: 30714375, each of which are incorporated herein by reference. In preferred embodiments, the presence of an analyte is determined indirectly via a label that is cleaved from the probe. In certain embodiments, in the presence of analyte, the sensor molecule no longer inhibits the restriction enzyme from recognizing the restriction site in the DNA template, and the DNA template is cleaved. The cleaved DNA template can then hybridize to a probe, which can have a florescent label and a quencher that are operably linked or an electrochemical label. In certain embodiments, the DNA template hybridized to the probe can be cleaved by one or more restriction enzymes. This cleavage can remove the quencher or the electroactive reporter from the probe, enabling the detection of an analyte and opening up a toehold DNA strand and generates an overhang of at least one, two, three, four, five, six, seven, eight, nine, ten, or more nucleotides in length on the unmodified DNA template strand, which serves as a toehold domain and nucleation site for another invading probe to initiate a toehold-mediated strand displacement reaction (TMSD). The result of this reaction is the displacement and accumulation of a label, preferably the fragment of the invading probe that contains the fluorophore or the electroactive reporter. The newly formed hybridized invading probe and DNA template enters a cycling reaction of cleavage by one or more restriction enzymes and then TMSD events.

In certain embodiments, hybridization of a probe, particularly the invading probe, to a nucleotide sequence, particularly the DNA template, may be achieved by any means that anneals the probe to the DNA template. In one embodiment, hybridization may be achieved by toehold-mediated strand displacement. Hybridization may be triggered by a probe annealing to a toehold sequence on a partially double stranded polynucleotide chain. Annealing of the toehold sequence on the partially double stranded polynucleotide chain to the probe may cause the strands of the partially double stranded polynucleotide chain to separate and the probe to hybridize to the polynucleotide sequence comprising the toehold. The strand that does not comprise the toehold sequence is displaced. It will generally be understood that the specificity of the hybridization reaction of the probe to the polynucleotide sequence may be governed thermodynamically by the sequence of the probe and/or the length of the toehold region.

Cleavage of the hybridized probe and polynucleotide sequence may result in the emission of a signal from the probe. Detection of the presence of an emitted signal may be indicative of the presence of an analyte in a sample. The intensity of the emitted signal may be measured relative to a reference signal. A reference signal may be a signal emitted from a sample with known analytes. A reference signal may also be a signal emitted from the same sample prior to the addition of an enzyme (i.e., the restriction enzyme can be added to the sample after the DNA template, sensor molecule, and appropriate reaction components) or prior to the removal or displacement of one or more probes. A reference signal may also be a signal emitted from a sample in the absence of hybridization of a probe to the polynucleotide sequence.

In certain embodiments, the DNA template sequence can possess a nucleotide spacer between the recognition site of the sensor molecule and the restriction site, which means that the subject invention can be used with virtually any aTF or aptamer without the requirement of overlapping sequences between the endonuclease's recognition site and an operator sequence, such as the DNA binding sequence of the aTF. In certain embodiments, 1, 2, 3, 4, 5, 6, 7, 8, 9, 10, 11, 12, 13, 14, 15, 16, 17, 18, 19, 20 or more can separate the recognition site of the sensor molecule and the restriction site.

Probe Design and Detection

In certain embodiments, probes can be designed to hybridize to a template DNA sequence, or portions thereof. In certain embodiments, the complementary nucleotide segment of the probe is 1, 2, 3, 4, 5, 6, 7, 8, 9, 10, 11, 12, 13, 14, 15, 16, 17, 18, 19, 20, 21, 22, 23, 24, 25, 30, 40, 50, or 100 base pairs long, or longer. In preferred embodiments, the complementary nucleotide segment of the probe is about 10 to about 50 base pairs longs. Furthermore, the probe (e.g., any herein, such as an invading probe) can be labeled with a fluorescent label (e.g., for use with a quencher label), electroactive label, or can be unlabeled. The probes can have an endonuclease binding site. The concentration of the probes can be optimized to promote the amplification reaction.

In certain embodiments, the probes herein can include any useful label, including fluorescent labels and quencher labels at any useful position in the nucleic acid sequence, such as, for example at the 3'- and/or 5'-terminus or within the loop structure of a probe. Exemplary fluorescent labels include a quantum dot or a fluorophore. Examples of fluorescence labels for use in this method includes fluorescein, 6-FAM™ (Applied Biosystems, Carlsbad, Calif.), TET™ (Applied Biosystems, Carlsbad, Calif.), VIC™ (Applied Biosystems, Carlsbad, Calif.), MAX, HEX™ (Applied Biosystems, Carlsbad, Calif.), TYE™ (ThermoFisher Scientific, Waltham, Mass.), TYE665, TYE705, TEX, JOE, Cy™ (Amersham Biosciences, Piscataway, N.J.) dyes (Cy2, Cy3, Cy3B, Cy3.5, Cy5, Cy5.5, Cy7), Texas Red® (Molecular Probes, Inc., Eugene, Oreg.), Texas Red-X, AlexaFluor® (Molecular Probes, Inc., Eugene, Oreg.) dyes (AlexaFluor 350, AlexaFluor 405, AlexaFluor 430, AlexaFluor 488, AlexaFluor 500, AlexaFluor 532, AlexaFluor 546, AlexaFluor 568, AlexaFluor 594, AlexaFluor 610, AlexaFluor 633, AlexaFluor 647, AlexaFluor 660, AlexaFluor 680, AlexaFluor 700, AlexaFluor 750), DyLight™ (ThermoFisher Scientific, Waltham, Mass.) dyes (DyLight 350, DyLight 405, DyLight 488, DyLight 549, DyLight 594, DyLight 633, DyLight 649, DyLight 755), ATTO™ (ATTO-TEC GmbH, Siegen, Germany) dyes (ATTO 390, ATTO 425, ATTO 465, ATTO 488, ATTO 495, ATTO 520, ATTO 532, ATTO 550, ATTO 565, ATTO Rho101, ATTO 590, ATTO 594, ATTO 610, ATTO 620, ATTO 633, ATTO 635, ATTO 637, ATTO 647, ATTO 647N, ATTO 655, ATTO 665, ATTO 680, ATTO 700, ATTO 725, ATTO 740), BODIPY® (Molecular Probes, Inc., Eugene, Oreg.) dyes (BODIPY FL, BODIPY R6G, BODIPY TMR, BOPDIPY 530/550, BODIPY 558/568, BODIPY 564/570, BODIPY 576/589, BODIPY 581/591, BODIPY 630/650, BODIPY 650/665), HiLyte Fluor™ (AnaSpec, Fremont, Calif.) dyes (HiLyte Fluor 488, HiLyte Fluor 555, HiLyte Fluor 594, HiLyte Fluor 647, HiLyte Fluor 680, HiLyte Fluor 750), AMCA, AMCA-S, Cascade® Blue (Molecular Probes, Inc., Eugene, Oreg.), Cascade Yellow, Coumarin, Hydroxycoumarin, Rhodamine Green™-X (Molecular Probes, Inc., Eugene, Oreg.), Rhodamine Red™-X (Molecular Probes, Inc., Eugene, Oreg.), Rhodamine 6G, TMR, TAMRA™ (Applied Biosystems, Carlsbad, Calif.), 5-TAMRA, ROX™ (Applied Biosystems, Carlsbad, Calif.), Oregon Green® (Life Technologies, Grand Island, N.Y.), Oregon Green 500, IRDye® 700 (Li-Cor Biosciences, Lincoln, Nebr.), IRDye 800, WellRED D2, WellRED D3, WellRED D4, and Lightcycler® 640 (Roche Diagnostics GmbH, Mannheim, Germany). In some embodiments, bright fluorophores with extinction coefficients >50,000 M$^{-1}$ cm$^{-1}$ and appropriate spectral matching with the fluorescence detection channels can be used.

In certain embodiments, a fluorescently labeled probe is included in a reaction mixture and a fluorescently labeled reaction product is produced. Fluorophores used as labels to generate a fluorescently labeled probe included in embodiments of methods and compositions of the present invention can be any of numerous fluorophores including, but not limited to, 4-acetamido-4'-isothiocyanatostilbene-2,2' disulfonic acid; acridine and derivatives such as acridine and acridine isothiocyanate; 4-amino-N-[3-vinylsulfonyl)phenyl]naphthalimide-3,5 disulfonate, Lucifer Yellow VS; N-(4-anilino-1-naphthyl)maleimide; anthranilamide, Brilliant Yellow; BIODIPY fluorophores (4,4-difluoro-4-bora-3a,4a-diaza-s-indacenes); coumarin and derivatives such as coumarin, 7-amino-4-methylcoumarin (AMC, Coumarin 120), 7-amino-4-trifluoromethylcoumarin (Coumaran 151); cyanosine; DAPDXYL sulfonyl chloride; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-4'-dimethylaminophenylazo)benzoic acid (DABCYL); 4-dimethylaminophenylazophenyl-4'-isothiocyanate (DABITC); EDANS (5-[(2-aminoethyl)amino]naphthalene-1-sulfonic acid), eosin and derivatives such as eosin isothiocyanate; erythrosin and derivatives such as erythrosin B and erythrosin isothiocyanate; ethidium such as ethidium bromide; fluorescein and derivatives such as 5-carboxyfluorescein (FAM), hexachlorofluorescenin, 5-(4,6-dichlorotriazin-2-yl)aminofluorescein (DTAF), 2',7'-dimethoxy-4',5'-dichloro-6-carboxyfluorescein (JOE) and fluorescein isothiocyanate (FITC); fluorescamine; green fluorescent protein and derivatives such as EBFP, EBFP2, ECFP, and YFP; IAEDANS (5-({2-[(iodoacetyl)amino]ethyl} amino)

naphthalene-1-sulfonic acid), Malachite Green isothiocyanate; 4-methylumbelliferone; orthocresolphthalein; nitrotyrosine; pararosaniline; Phenol Red; B-phycoerytnin; o-phthaldialdehyde; pyrene and derivatives such as pyrene butyrate, 1-pyrenesulfonyl chloride and succinimidyl 1-pyrene butyrate; QSY 7; QSY 9; Reactive Red 4 (Cibacron® Brilliant Red 3B-A); rhodamine and derivatives such as 6-carboxy-X-rhodamine (ROX), 6-carboxyrhodamine (Rhodamine 6G), rhodamine isothiocyanate, lissamine rhodamine B sulfonyl chloride, rhodamine B, rhodamine 123, sulforhodamine B, sulforhodamine 101 and sulfonyl chloride derivative of sulforhodamine 101 (Texas Red); N,N,N', N-tetramethyl-carboxyrhodamine (TAMRA); tetramethyl rhodamine; tetramethyl rhodamine isothiocyanate (TRITC); riboflavin; rosolic acid and terbium chelate derivatives. In certain embodiments, the concentration of the fluorescent probe in the compositions and method of use is about 0.01 µM to about 100 µM, about 0.1 µM to about 100 µM, about 0.1 µM to about 50 µM, about 0.1 µM to about 10 µM, or about 1 µM to about 10 µM. In certain embodiments, the concentration of the fluorescent probe is about 0.01 µM, about 0.1 µM, about 1 µM, 1.1 µM, 1.2 µM, about 1.25 µM, about 1.3 µM, about 1.4 µM, about 1.5 µM, about 1.6 µM, about 1.7 µM, about 1.8 µM, about 1.9 µM, about 2 µM, about 2.5 µM, about or 5 µM.

Exemplary quencher labels include a fluorophore, a quantum dot, a metal nanoparticle, and other related labels. Suitable quenchers include Black Hole Quencher®-1 (Biosearch Technologies, Novato, CA), BHQ-2, Dabcyl, Iowa Black® FQ (Integrated DNA Technologies, Coralville, IA), IowaBlack RQ, QXL™ (AnaSpec, Fremont, CA), QSY 7, QSY 9, QSY 21, QSY 35, IRDye QC, BBQ-650, Atto 540Q, Atto 575Q, Atto 575Q, MGB 3' CDPI3, and MGB-5' CDPI3. In one instance, the term "quencher" refers to a substance which reduces emission from a fluorescent donor when in proximity to the donor. In preferred embodiments, the quencher is within 1, 2, 3, 4, 5, 6, 7, 8, 9, 10, 11, 12, 13, 14, 15, 16, 17, 18, 19, 20, 25, or 30 nucleotide bases of the fluorescent label. Fluorescence is quenched when the fluorescence emitted from the fluorophore is detectably reduced, such as reduced by 10%, 20%, 30%, 40%, 50%, 60%, 70%, 80%, 90%, 95%, 99% or more. Numerous fluorophore quenchers are known in the art, including, dabcyl; sulfonyl chlorides such as dansyl chloride; and Black Hole Quenchers BHQ-1, BHQ-2 and BHQ-3.

In certain embodiments, an electroactively labeled probe is included in a reaction mixture and an electroactively labeled reaction product is produced. Electroactive reporters can be used as labels to generate an electroactively labeled probe or oligonucleotide included in embodiments of methods and compositions of the present invention can be any of numerous Electroactive reporters including, but not limited to methylene blue, Anthraquinone, Ru(bpy)2dppz2+, Ru(phen)2dppz2+, Ferrocene derivative, hematoxylin, magnetic bead, QD, biotin-advinHRP, nano composite and ferrocene. In certain embodiments, the concentration of the electroactive probe in the compositions and method of use is about 0.01 µM to about 100 µM, about 0.1 µM to about 100 µM, about 0.1 µM to about 50 µM, about 0.1 µM to about 10 µM, about 1 µM, about 1.25 µM, about 1.5 µM to about 10 µM. In certain embodiments, the concentration of the electroactive probe is about 0.01 µM, about 0.1 µM, about 1 µM, about 1.1 µM, about 1.2 µM, about 1.3 µM, about 1.4 µM, about 1.5 µM, about 1.6 µM, about 1.7 µM, about 1.8 µM, about 1.9 µM, about 2 µM, about 2.5 µM, or about 5 µM.

Other labels can be used in the subject in invention, including those that permit colorimetric, and chemiluminescent or fluorescent detection. For example, biotin or digoxin are well-known in the art and can be used in conjunction with, anti-digoxin antibodies and streptavidin that are couple to alkaline phosphatase, horseradish peroxidase, or fluorescein or rhodamine, to permit colorimetric, and chemiluminescent or fluorescent detection.

Any detection method or system operable to detect a labeled nucleotide can be used in methods according to embodiments of the present invention and such appropriate detection methods and systems are well-known in the art. In certain embodiments, the analyte can be detected indirectly via a cleaved probe in which the labelled end of the probe is released as a cleavage product. Detection of the cleaved product may be performed by a method selected from the group consisting of gel electrophoresis, mass spectrometry, Fluorescence Resonance Energy Transfer (FRET), lateral flow assays, colorimetric assays, luminescent assays, and electrochemical detection methods, such as differential pulse voltammetry. A signal from the fluorescently labeled reaction product is detected, for instance, using a photodiodes.

In preferred embodiments, the presence of an analyte is determined indirectly via a label that is cleaved from a probe. In certain embodiments, in the presence of analyte, the sensor molecule no longer inhibits the restriction enzyme from recognizing the restriction site in the DNA template, and the DNA template is cleaved. The cleaved DNA template can then hybridize to a probe, which can have a florescent label and a quencher that are operably linked or an electrochemical label. In certain embodiments, the DNA template hybridized to the probe can be cleaved by one or more restriction enzymes. This cleavage can remove the quencher or the electroactive reporter from the probe, opening up a toehold DNA strand and generates an overhang of at least one, two, three, four, five, six, seven, eight, nine, ten, or more nucleotides in length on the unmodified DNA template strand, which serves as a toehold domain and nucleation site for another invading probe to initiate a toehold-mediated strand displacement reaction (TMSD).

The result of this reaction is the displacement and accumulation of a label, preferably the fragment of the invading probe that contains the fluorophore or the electroactive reporter. The newly formed hybridized invading probe and DNA template enters a cycling reaction of cleavage by one or more restriction enzymes and then TMSD events. Throughout the cycles, the total amount of invading probe can decrease and the amount of labelled, cleaved invading probe can increase. Each cycle results in the accumulation of the displaced labelled product on the cleaved invading probe. The labelled signal can be measured across time or endpoint. The rate of the reaction is influenced by the concentration of the DNA template. The rate of the reaction and final intensity of the label can depend on the concentration of invading probe.

The detection of this cleaved label can be performed in using a variety of well-known methods. Examples of detection methods include electroactive assay, fluorescent assay, or a lateral-flow assay. Upon restriction enzyme cleavage, a fluorophore or electroactive reporter can be released. Example of the use of electroactively labelled probes and methods of detections of said probes are described in the art, for example, in U.S. Pat. No. 8,975,025, which is in incorporated by reference in its entirety.

In a lateral flow assay, for example, the sample could be passed across a surface that has a recognition element, including nucleic acids, or, preferably, antibodies. The lateral-flow assay can be either a sandwich or competitive assay. In certain embodiments, the cleaved label that results from the presence of a target nucleotide would bind with antibody-conjugated nanoparticles, flow through the control band, and get stopped by the test band. Therefore, the test band would appear in the presence of target. In the absence of analyte, the probe is not cleaved, and it would bind to the antibody-conjugated nanoparticles and be trapped by the control band.

Sensor Molecule

In certain embodiments, the sensor molecule is an allosteric protein or an aptamer. The sensor molecule can be any natural or engineered protein that has allosteric behavior and comprises at least one effector binding domain and at least one nucleic acid binding domain. In certain embodiments, the sensor molecule can be monomer or a multimer. The effector binding domain can bind to a target analyte and inhibit a nucleic acid binding domain from binding to a DNA template. The aptamer can be any nucleic acid sequence that has at least one analyte binding domain and is complementary to at least 4, 5, 6, 7, 8, 9, 10, 11, 12, 13, 14, 15, 16, 17, 18, 19, 20, or more base pairs in a DNA template. There can be gaps, substitutions, deletions, or other nucleic modifications so long as the aptamer can hybridize to a DNA template. At least 1, 2, 3, 4, 5, 6, 7, 8, 9, 10, 11, 12, 13, 14, 15, 16, 17, 18, 19, 20, or more nucleic acids can be substituted, deleted, or can be in a gap region of the complementary region. In certain embodiments, the sensor molecules can be encoded by vectors, such as plasmid vectors, cosmid vectors, bacterial vectors, or bacteriophage vectors; all of which comprise a recombinant polynucleotide that expresses a polypeptide. Expressed proteins can contain tags to facilitate downstream purification. Tags include, but are not limited to, polyhistidine tag, FLAG tag, GST tag and Myc tag. Further steps to remove the tags from the protein may be needed and are well-known in the art.

In certain embodiments, the sensor molecule can be an allosteric transcription factor (aTF), for instance a eukaryotic or prokaryotic aTF. In various embodiments, the sensor molecule can be a member of, for example, AraC/XlyS family, ArgR family, ArsR/SmtB family, AsnC/Lrp family, Crp/Fnr family, DeoR family, DtxR family, Fur family, GntR family, IclR family, Lad family, LuxR family, LysR family, MarR family, MerR family, MetJ family, ModE family, PadR family, TetR family, Xre family. Examples of TetR family include but are not limited to TetR, MphR, NemR, PaaR, SaaR, RutR, SczA, RolR, QdoR, PsbI, PmeR, CymR, ComR, BetI, and TtgR. The sensor molecule can be a naturally occurring (wild-type) or an engineered aTF.

Additional or alternative illustrative aTFs are found in Ramos et al. Microbiology and Molecular Biology Reviews, June 2005, p. 326-356 and Tropell, et al. *Microbiol Mol Biol Rev.* 2004 September; 68(3):474-500, the contents of which are hereby incorporated by reference in their entireties.

In certain embodiments, one, two, three, four, five, six, seven, or more aptamers can be used as a sensor molecule. In certain embodiments, there is provided herein a sensor for detecting the presence of a target analyte, comprising an aptamer probe having region that can bind to an analyte. Aptamers of the invention are preferably specific for a particular analyte. Aptamers can have diagnostic, target validation and therapeutic applications. The specificity of the binding is defined in terms of the dissociation constant Kd of the aptamer for its ligand. Aptamers can have high affinity with Kd range similar to antibody (pM to nM) and specificity similar/superior to antibody. An aptamer will typically be between about 10 and about 100 nucleotides in length. Aptamers configured to bind to specific target analytes can be selected, for example, by synthesizing an initial heterogeneous population of oligonucleotides, and then selecting oligonucleotides within the population that bind tightly to a particular target analyte. Such aptamers may be presently extant in the art or presently used commercially, or may be developed by techniques now common in the field of immunology. Aptamer sequences are well known in the art. The aptamers can be chemically synthesized by a commercial supplier. As well, they can be purchased from companies that developed them. Also, one can generate their own aptamer using Systematic evolution of ligands by exponential enrichment (SELEX), which is an in vitro selection process well-known in the art. Once an aptamer that binds to a particular target analyte has been identified, it can be replicated using a variety of techniques known in biological and other arts, for example, by cloning or chemical synthesis and polymerase chain reaction (PCR) amplification followed by transcription or in vitro transcription.

In certain embodiments can be present in the compositions or methods at a concentration of about 1 nM to about 1000 nM, about 10 nM to about 500 nM, about 100 nM to about 500 nM, about 200 nM to about 300 nM, about 100 nM, about 200 nM, about 225 nM, about 250 nM, about 275 nM, about 300 nM, or about 400 nM.

Kits

In certain embodiments, the present compositions and methods of use can further be provided in a kit. The kit can include one or more of the following: one or more restriction enzymes, one or more DNA templates, one or more sensor molecules, one or more invading probes, and other reagents (e.g., any described herein, such as enzymes, buffers, or enhancing agents), particularly reagents that one skilled in the art would recognize as necessary or beneficial for Toehold-mediated Strand Displacement reactions, and instructions for use (e.g., such as those including any method described herein). Each component of the kit can be packaged separately or together. In one instance, the components are packaged together to allow for a single chamber or single test tube reaction.

Enzymes

In certain embodiments, one or more enzymes can be used, including a plurality of endonucleases. The restriction enzyme can generate an overhang at the 3' or 5' end of the DNA template that is at least three, four, five, six, seven, or eight nucleotides in length. In certain embodiments, the restriction enzyme can be monomer or a multimer. In preferred embodiments, one or more Type IIS endonucleases can be used. Exemplary Type IIS endonuclease enzymes include AarI, Acc36I, AclWI, AcuI, AjuI, AloI, Alw26I, AlwI, ArsI, AsuHPI, BaeI, BarI, BbsI, BbsI-HF®, BbvI, BccI, BceAI, BcgI, BciVI, BcoDI, BfuAI, BfuI, BmrI, BmsI, BmuI, BpiI, BpmI, BpuEI, BsaI-HF®v2, BsaXI, BseII, Bse3DI, BseGI, BseMI, BseMII, BseNI, BseRI, BseXI, BsgI, BslFI, BsmAI, BsmBI-v2, BsmFI, BsmI, Bso31I, BspCNI, BspMI, BspPI, BspQI, BspTNI, BsrDI, BsrI, Bst6I, BstF5I, BstMAI, BstV1I, BstV2I, BsuI, BtgZI, BtsCI, BtsI-v2, BtsIMutI, BveI, CseI, CspCI, Eam1104I, EarI, EciI, Eco31I, Eco57I, Esp3I, FaqI, FauI, FokI, GsuI, HgaI, HphI, HpyAV, LguI, LmnI, Lsp1109I, LweI, MboII, MlyI, MmeI, MnlI, Mva1269I, NmeAIII, PaqCI, PciSI, PctI, PleI, PpsI, PsrI, SapI, SchI, SfaNI, TaqII, TspDTI, and TspGWI; or any of isoschizomers thereof.

In certain embodiments, the one or more enzymes can be at a concentration of about 1 U/mL to about 1000 U/mL, about 20 U/mL to about 500 U/mL, about 50 U/mL to about 250 U/mL, or about 100 U/mL.

Buffering Agents, Cofactors, Metals, Proteins and Salts

Buffering agents and salts useful in the present invention provide appropriate stable pH and ionic conditions for nucleotide hybridization, toehold-strand mediate displacement, restriction enzyme cleavage and/or allosteric transcription factor folding and binding to the DNA template. A wide variety of buffers and salt solutions and modified buffers are known in the art that can be useful in the present invention, including agents not specifically disclosed herein. Preferred buffering agents include, but are not limited to, Tris-HCl, NaCl, $MgCl_2$, and BSA. Preferred salt solutions include, but are not limited to solutions of, potassium acetate, potassium sulfate, potassium chloride, ammonium sulfate, ammonium chloride, ammonium acetate, magnesium chloride, magnesium acetate, magnesium sulfate, manganese chloride, manganese acetate, manganese sulfate, sodium chloride, sodium acetate, lithium chloride, and lithium acetate.

The buffering agents can be present in any concentration. In some embodiments, the buffering agent is present in an amount from about 0.01 nM to about 400 mM, about 0.05 nM to about 200 mM, or about 0.1 nM to about 100 mM or about 50 nM. One of skill in the art will appreciate that other concentrations of buffer are useful in the present invention.

In certain embodiments, the compositions and methods can further comprise cofactors, metals, and proteins that permit for the functioning, stability, and folding of restriction enzymes and/or allosteric proteins.

Methods of Use

In certain embodiments, the endonuclease (restriction enzyme), a DNA template, a sensor molecule, and an invading probe can be used to detect any analyte of interest in a sample. The analyte can be a small molecules, metabolites, or precursors thereof, such as antibiotics, aromatic compounds, quorum sensing molecules, or metals. In preferred embodiments, the analyte can be metals or cation thereof such as, for example, Hg, Cu, Ag, Au, Zn, As, Ni, Co, Cd, Pb, Fe, Ni, Mn, Cd, thus $Hg^{2+}$, $Cu^+$, $Ag^+$, $Au^+$, $Zn^{2+}$, $As^{3+}$, $Ni^{2+}$, $Co^{2+}$, $Cd^{2+}$, $Pb^{2+}$, $Fe^{2+}$, $Ni^{2+}$, $Mn^{2+}$, and $Cd^{2+}$; aromatic molecules such as, for example, benzoate, n-toluate, toluene, xylene, chlorinated phenols, p-toluenesulfonate, pentachlorophenol, trichlorophenol, salicylate, cis-muconate, 2-chloro-cis, and cis-muconate; antibiotics such as, for example, tetracyclines, macrolides, chloramphenicol, actinorhodin, ethionamine boosters, simocyclinone, kanamycin, streptomycin, and nalidixic acid; and other small molecules such as, for example, metabolites, toxins, molecules derived from esters, hormones, and pesticides.

In particular, the compositions and methods allow sensor molecules to control the cleavage of nucleic acid sequences. The recognition ability of the sensor molecule allows one, particular an aTF or an aptamer, to trigger a simpler, more affordable, rapid, modular and programmable nucleic-acid based circuit reaction. In certain embodiments, a signal transducer and amplifier circuit that, as a standalone, relies on the cycling cleavage of a DNA template by an endonuclease is provided. This cleavage generates a toehold region on the template, which is then used as a nucleation site for hybridization of an invading probe. Then, the invading probe initiates a strand displacement reaction that ends in the displacement of one of the original template strands. Importantly, this newly-formed double stranded fragment contains the DNA recognition site of the endonuclease. Thus, this fragment can be cleaved and the toehold domain is formed again. At a constant concentration of endonuclease, the kinetics of the cycling reaction is dependent on the concentration of the DNA template and the concentration and sequence of the Invading Probe. The Invading Probe can be chemically modified with chemical labels for direct detection of the cleaved product by colorimetric, fluorescent or electrochemical methods.

The actuation of the cycling reaction can depend on the accessibility of the endonuclease to its DNA recognition site. In certain embodiments, the compositions and methods can be used to impede the access of the endonuclease to its recognition site in the absence of a sensor biomolecule's cognate ligand.

In preferred embodiments, compositions and methods can be designed using aTFs or aptamers as sensor molecules. An aTF can compete with the endonuclease for the same, overlapping or adjacent DNA sequence. An aptamer can make the restriction site unrecognizable by the restriction enzyme. In the absence of the ligand, the aTF or aptamer inhibits the DNA from endonuclease cleavage. When the ligand is present and binds to the aTF, the aTF undergoes a conformational change and dissociates from the DNA, allowing the endonuclease to cleave and start the signal amplification cycle. When the ligand is present and binds to the aptamer, the aptamer can be released from the DNA template and the DNA template can hybridize to an invading probe. The formation of this product permits the recognition by the restriction enzyme of a restriction site in the DNA template, allowing the endonuclease to cleave and start the signal amplification cycle.

In certain embodiments, compositions and methods can be designed to switch secondary structures of the DNA template in an aptasensor. The dissociation of an aptamer upon binding to its ligand allows a strand displacement reaction that generates the endonuclease's double-stranded recognition site, which would be otherwise 'sequestered' in a loop structure. In certain embodiments, a restriction enzyme, such as HgaI, binds to its recognition site in a double stranded DNA molecule. The DNA template is a structure that comprises a complementary sequence to the aptamer adjacent to a hairpin (i.e. stem-loop). The restriction enzyme recognition site can be sequestered in the loop region of the template, which is single stranded and thus inaccessible to the restriction enzyme. When a cognate ligand binds to the aptamer, the aptamer can dissociate from the DNA template sequence. The DNA template sequence then can hybridize to the Invading probe at the template's aptamer complementary sequence (i.e., the invading probe and the aptamer can have complementary base pairs). The full complementarity between template and invading probe allows the opening of the template's stem and formation of a double-stranded intermediary (S-IP), which contains the restriction enzyme recognition site, now accessible to the restriction enzyme. From this point, the cycling TMSD and cleavage reaction occur, as previously explained.

The subject invention has advantageous properties that can utilize a type IIS endonuclease that functions both for transducing the sensor/ligand binding event and sustaining strand displacement reactions for signal amplification. Moreover, the type IIS endonuclease that is used in the subject invention can cleave double-stranded DNA base pairs downstream of its recognition site. Importantly, the sequence between the recognition site and the cleaving site can be any sequence, which means that the subject invention can be used with virtually any aTF or aptamer without the requirement of overlapping sequences between the endonuclease's recognition site and the operator sequence, such as the DNA binding sequence of the aTF or aptamer. Also, as the cleavage generates a toehold domain in the DNA, we utilize a labelled probe that carries out strand displacement reactions so it is continuously cleaved and displaced by the endonuclease and the probe, respectively, already in the system. This allows the simple, one-pot, real-time detection of small molecules.

The subject toehold-mediated strand displacement-based circuit can be actuated by the cognate ligands (analytes) of sensor molecules, particular aTFs and aptamers. The sensor molecules have a quantitative response to ligands in varying dynamic ranges and can be integrated in one-pot assays, making the method simple and fast. Moreover, the method is highly modular and programmable, as one can design biosensors for different small molecules under the same principle. Finally, the sensitivity and kinetics can be fine-tuned by adjusting the concentration of the sensor molecule, and the concentrations and sequences of the template DNA and the Invading Probe.

In certain embodiments, the cycling of nucleic acids using successive restriction enzyme digests and hybridization of the invading probe to a template can be ended by, for example, deactivating the restriction enzymes by, for example, temperature change, adding of salts or other enzymes, changing the pH until the restriction enzyme is deactivated, by blocking the restriction enzyme recognition site, by, for example, adding competing DNA strands that hybridize with the invading probe or the template, or when there is no remaining uncleaved invading probe.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Example 1—End-Point Detection of Tetracycline in Water

In the example, the scheme provided in FIG. 1 is used to detect the antibiotic Tetracycline (Tc) spiked into a water sample via a fluorescent signal.

The first step to implement the method is to determine the binding sequence of the ligand-responsive allosteric protein. In this example, the detection of Tetracycline is achieved via TetR, a natural aTF that binds to Tetracycline and to the DNA sequence $TetO_1$ and $TetO_2$. Hence, the DNA fragment S will consist of the HgaI binding sequence immediately followed by $TetO_1$. Double stranded S can be formed by annealing two complementary oligonucleotides. Next, the sequence of the probe IP should consist of the complementary sequence of the cleaved strand that contains the overhang. In this case, IP is labelled with a fluorophore FAM on the 5' and a quencher BHQ-1 on the 3'.

The DNA sequences utilized in this example are shown in Table 1:

TABLE 1

| Name | Sequence (5' -> 3') |
|---|---|
| TetR*<br>SEQ ID NO: 1 | ATGAGTCGGTTAGACAAGAGTAAAGTGATTAATTCGGCTCTCGAACTGCT<br>GAATGAAGTTGGGATTGAGGGGTTGACTACCCGCAAATTAGCACAGAAAC<br>TTGGCGTAGAACAGCCAACTCTTTACTGGCACGTTAAGAATAAGCGGGCC<br>CTTCTTGATGCGCTTGCCATCGAGATGCTGGACCGCCATCACACACACTT<br>TTGCCCATTAGAAGGGGAGTCGTGGCAGGATTTCTTACGGAATAATGCCA<br>AGTCTTTCCGGTGCGCTCTTCTTAGCCATCGTGACGGTGCAAAGGTACAT<br>TTAGGCACGCGCCCGACCGAAAAACAGTACGAAACCTTAGAAAACCAGCT<br>TGCCTTTCTGTGTCAACAGGGTTTCAGCCTCGAAAATGCGTTATACGCTC<br>TGTCGGCCGTAGGCCACTTTACGCTCGGGTGCGTCCTCGAGGACCAAGAG<br>CACCAGGTCGCTAAGGAGGAGCGGGAGACCCCAACCACAGATAGTATGCC<br>ACCATTGTTACGTCAAGCAATCGAGTTGTTTGATCACCAAGGTGCGGAGC<br>CTGCATTTCTTTTTGGTTTAGAACTGATTATCTGTGGCCTTGAAAAGCAG<br>TTGAAATGCGAAAGCGGGTCCTGACATCATCATCATCATCAT |
| dsDNA template<br>(S)^<br>SEQ ID NO: 2 | ATAAA<u>GACGC</u>TCCCTATCAGTGATAGAGA |
| dsDNA template<br>complementary (S)<br>SEQ ID NO: 3 | TCTCTATCACTGATAGGGAGCGTCTTTAT |
| Invading Probe<br>(IP)<br>SEQ ID NO: 4 | FAM-ATAAAGACGCTCCCTATCAGTGA-BHQ |

*TetR sequence was inserted in plasmid pET-28a and expressed E. coli BL21 DE3. Purification and concentration were performed through His-Tag affinity chromatography and centrifuge filtration, respectively.
^Underlined is the recognition sequence of HgaI and the TetR DNA binding sequence (TetO1) is in bold.

Figure 7A:
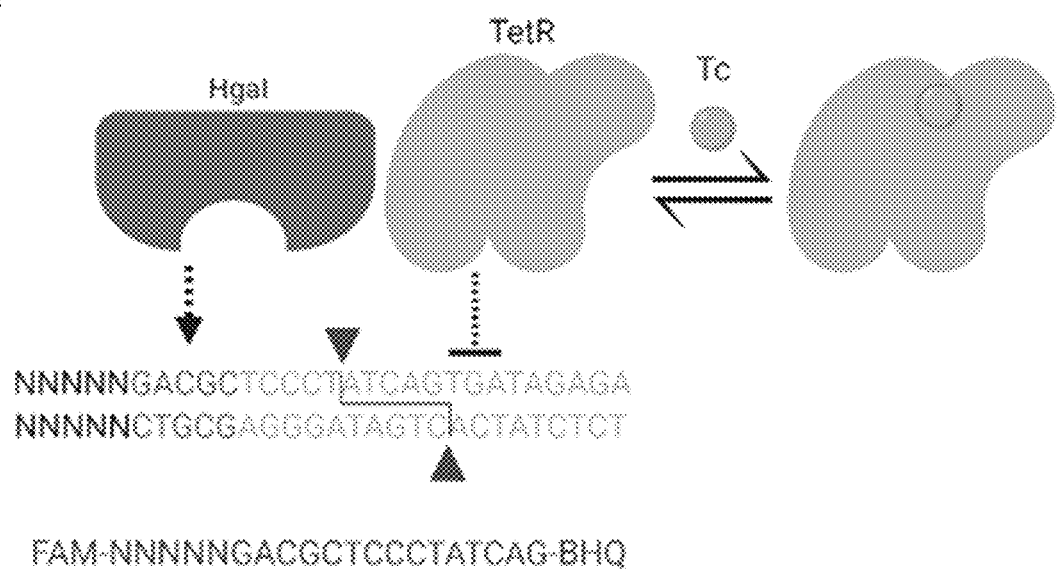
FIGS. 7A-7B show demonstrations that endonuclease-mediated toehold-mediated strand displacement (TMSD) reactions can be negatively regulated (repressed) by TetR and derepressed by tetracycline (Tc).
Figure 7B:
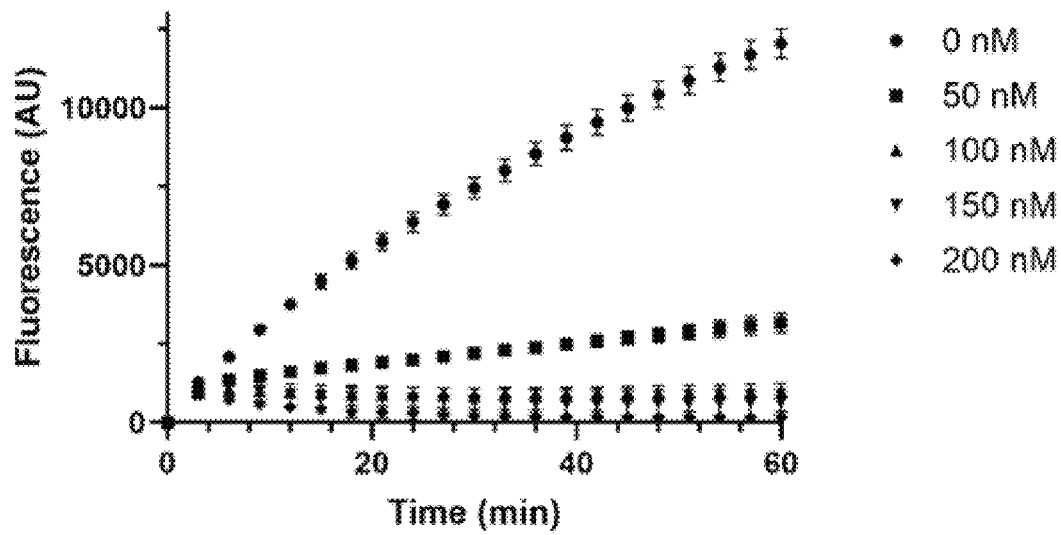

In this example, TetR was obtained by recombinant expression in E. coli and purified using affinity chromatography. After this, it is necessary to determine the concentration of the aTF required to repress the cleavage of $TetO_1$ by HgaI and the subsequent Toehold-mediated Strand Displacement reactions. The concentration of the aTF may vary depending on their affinity and binding constants for the DNA. In this example, titration of TetR against S showed that a 2-fold excess was enough to repress the overall reaction by >98% (FIG. 7B). This titration was performed as indicated in the formulation below, with the sample being replaced with ultrapure water and with varying final concentrations of TetR in the range of 50-500 nM.

The formulation of the reaction is shown in Table 2:

TABLE 2

| Component | Stock Concentration | Volume (uL) | Final concentration |
|---|---|---|---|
| S | 1 uM | 0.5 | 50 nM |
| TetR Dimer (aTF) | 2.5 uM | 1 | 250 nM |
| IP | 10 uM | 1.25 | 1.25 uM |
| Water | — | to 10 uL | — |
| NEBuffer 1.1 | 10X | 1 | 1X |
| Sample | — | 0-5.75 | — |
| HgaI | 2000 U/mL | 0.5 | 100 U/mL |
| Final | — | 10 uL | — |

Figure 8:
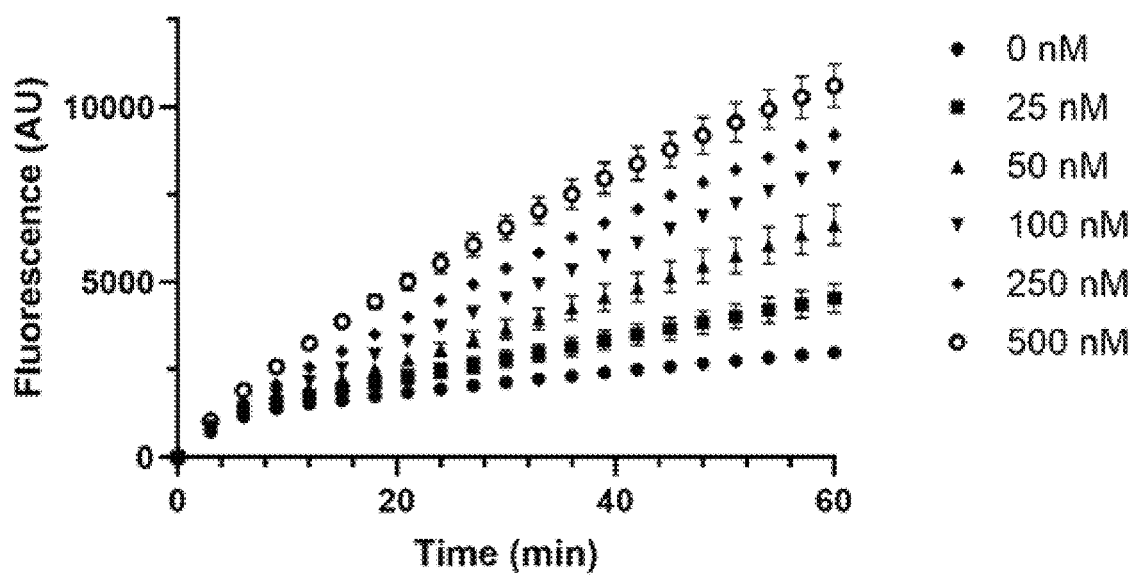
FIG. 8 shows a demonstration that the TetR-based biosensor responds to different concentrations of tetracycline (0 nM, 25 nM, 50 nM, 100 nM, 250 nM, and 500 nM).

Induction of the reactions at 37° C. with different concentrations of Tetracycline in the 25-500 nM range according to the formulation showed in the previous table generated different fluorescence intensities (FIG. 8).

It is to note that because the recognition site of HgaI is separate from the aTF binding sequence, and the cleavage site 5 and 10 nucleotides downstream on the 3' and 5' strand, respectively, is not constrained by any specific sequence, this method can be used with virtually any allosteric protein or aTF/ligand. In this case, it will be only necessary to change the allosteric protein/aTF and its cognate binding DNA sequences specific for said protein in S and IP.

A typical assay for small molecules using the method, parts and compositions presented herein would consist of the preparation of a reaction according to the formulation in the table above, followed by incubation at the working temperature of the restriction enzyme and measurement of the signal.

Example 2—Signal Transduction and Amplification Circuit

Figure 2:
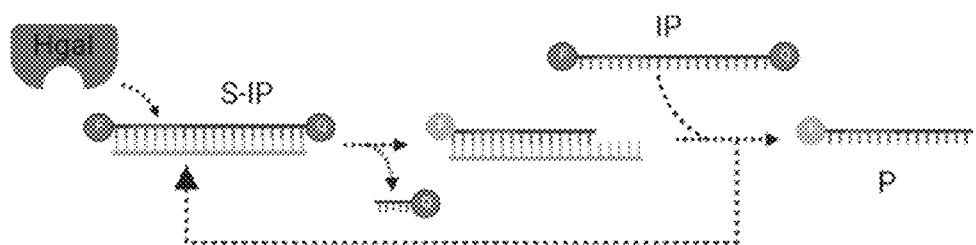
FIG. 2 shows an illustration of the standalone signal amplification circuit. The circuit has three main components: the type IIS restriction enzyme HgaI, the DNA intermediary (S-IP) and the Invading Probe (IP).

This example demonstrates the mechanism of the standalone circuit (FIG. 2). In this example, the Type IIS restriction enzyme used is HgaI, which recognizes asymmetric DNA sequences, cleaves outside of its recognition site and generates a 5-nucleotide long toehold on the 5' end of a double stranded fragment starting 5 base pairs downstream of its recognition site. The Invading Probe (IP) used is an oligonucleotide fully complementary to the strand where the toehold domain is generated in the DNA template. The IP contains the HgaI recognition site near its 5' end. The IP is chemically modified with the fluorophore 6-Carboxyfluorescein (6-FAM) and the quencher Black Hole Quencher 1 (BHQ-1) on the 5' and 3' ends, respectively. The DNA template (S-IP) in this example is a double-stranded DNA fragment composed of an unmodified strand hybridized with IP. It could as well be a double-stranded unmodified DNA fragment containing the HgaI recognition site.

Figure 3:
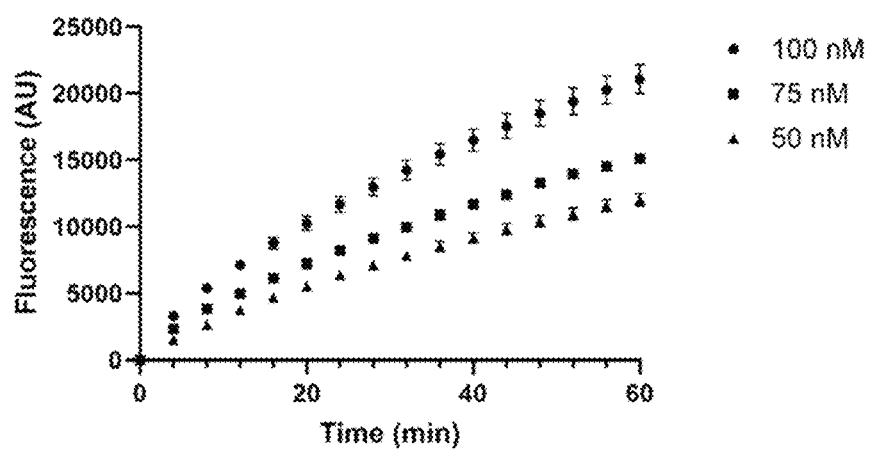
FIG. 3 shows a demonstration that the signal amplification circuit is dependent on the concentration of the DNA template (S). The reactions have a final volume of 10 uL and are composed of: 1.25 uM of IP, 100 U/mL of HgaI and varying concentrations of DNA template (S) (50 nM, 75 nM, and 100 nM).
Figure 4:
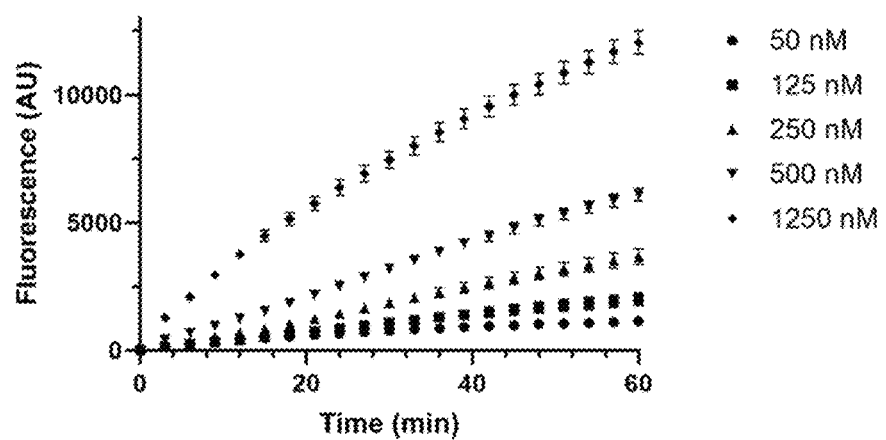
FIG. 4 shows a demonstration that the signal amplification circuit is dependent on the concentration of Invading Probe (IP). The reactions have a final volume of 10 uL and are composed of: 50 nM of DNA template (S), 100 U/mL of HgaI and varying concentrations of Invading Probe (IP) (50 nM, 125 nM, 250 nM, 500 nM, and 1250 nM).

In a system (under adequate reaction conditions) with HgaI, the DNA template, and the IP; HgaI binds to its recognition site and cleaves the DNA template. This cleavage releases the BHQ-1 label from IP and generates a 5' overhang of five nucleotides in length on the unmodified DNA strand, which serves as a toehold domain and nucleation site for the Invading Probe (IP) to initiate a toehold-mediated strand displacement reaction (TMSD). The result of this reaction is the displacement and accumulation of P, the fragment of the IP that contains the fluorophore. The newly formed S-IP enters a cycling reaction of cleavage by HgaI and TMSD events. Throughout the cycles, the total amount of IP decreases and P increases. Each cycle results in the accumulation of the displaced fluorescent product P, which fluorescent signal can be measured across time or endpoint. The rate of the reaction is influenced by the concentration of the DNA template (FIG. 3). As well, the rate of the reaction and final fluorescence intensity is dependent on the concentration of IP (FIG. 4).

Example 3—aTF-Based Biosensor

This example demonstrates the regulation (repression and derepression) of the circuit using allosteric Transcription Factors and their cognate ligands (FIG. 1). In this example, the Type IIS restriction enzyme used is HgaI, which recognizes asymmetric DNA sequences, cleaves outside of its recognition site and generates a 5-nucleotide long toehold on the 5' end of a double stranded fragment starting 5 base pairs downstream of its recognition site. The DNA template (S) is a double-stranded unmodified DNA fragment containing the HgaI recognition site immediately upstream of an operator sequence. The Invading Probe (IP) used is an oligonucleotide fully complementary to the strand where the toehold domain is generated in the DNA template. The IP contains the HgaI recognition site near its 5' end. The IP is chemically modified with the fluorophore 6-Carboxyfluorescein (6-FAM) and quencher Black Hole Quencher 1 (BHQ-1) on the 5' and 3' ends, respectively.

This example considers a system consisting of S, IP, HgaI, aTF and the ligand of aTF. In the absence of the cognate Ligand of aTF, the aTF binds to the operator sequence in S and inhibits HgaI from cleaving the DNA template. If the ligand is present, it binds to the aTF and the latter undergoes a conformational change that decreases its affinity for the operator, causing its dissociation from the template S. This allows HgaI to bind to its recognition site in S, cleave the operator sequence and generate a product that lacks the full operator sequence and contains a toehold domain. The IP binds to the toehold domain and start a TMSD reaction, which product is S-IP. The signal amplification cycle can then occur, as explained in Example 2.

Figure 9A:
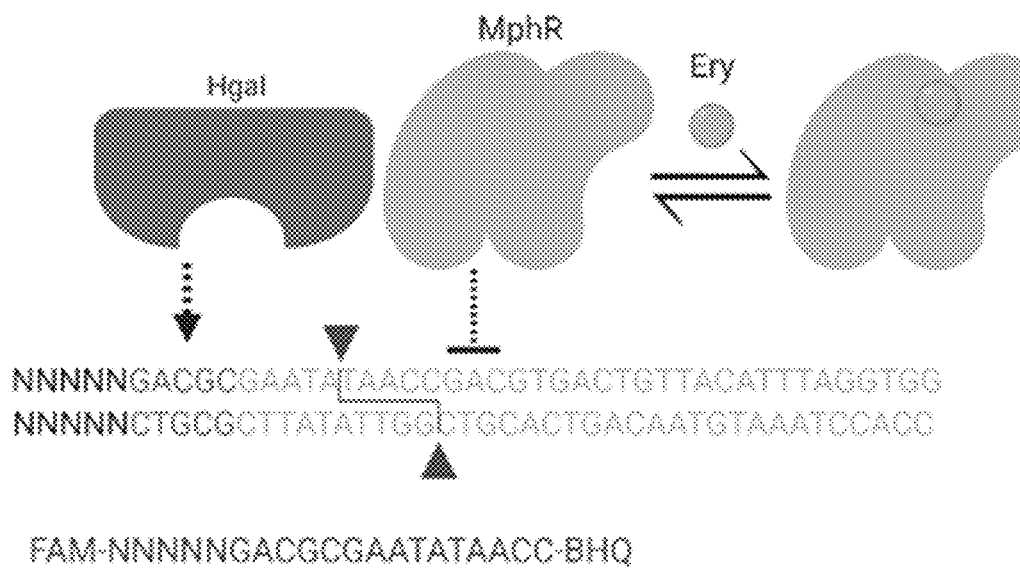
FIGS. 9A-9B show demonstrations that endonuclease-mediated toehold-mediated strand displacement (TMSD) reactions can be negatively regulated (repressed) by MphR and derepressed by erythromycin (Ery).
Figure 9B:
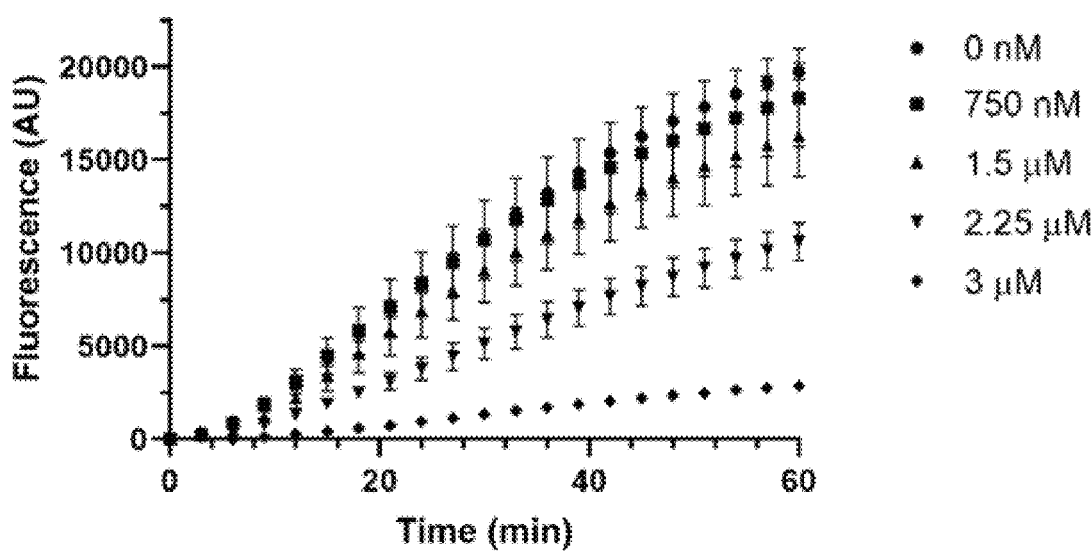
Figure 10:
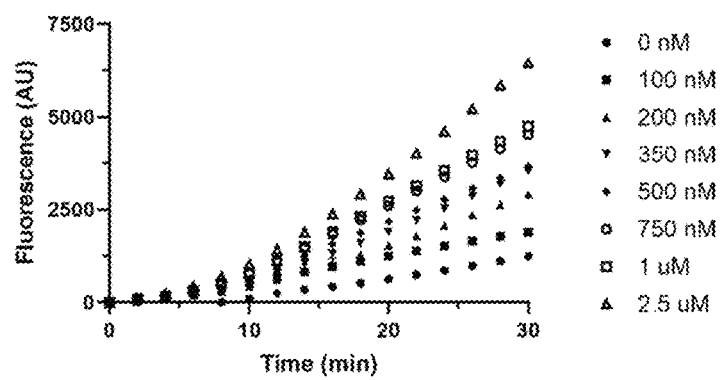
FIG. 10 shows a demonstration that the MphR-based biosensor responds to different concentrations of erythromycin (0 nM, 100 nM, 200 nM, 350 nM, 500 nM, 750 nM, 1 uM, and 2.5 uM).

Here we present two biosensors built with the described mechanism above. As shown in FIGS. 7A-7B, the aTF TetR (SEQ ID NO: 21) can be used to build a tetracycline biosensor using its corresponding operator sequence in the DNA template and partially in the IP (SEQ ID NO: 19). Increasing concentrations of TetR decrease the rate of the reaction as there is less DNA template accessible to HgaI. When the system is repressed by a given concentration of TetR, it can be derepressed by the ligand tetracycline. The rate of the reaction is proportional to the concentration of tetracycline within a certain concentration range (FIG. 8). Similarly, a circuit using the aTF MphR (SEQ ID NO: 22) with its corresponding operator sequence (SEQ ID NOs: 17 and 18) in the DNA template and partially in the IP (SEQ ID NO: 20) can be used to sense macrolides. In absence of erythromycin (a macrolide molecule), increasing concentrations of MphR result in a decrease of the reaction rate (FIGS. 9A-9B). At a fixed concentration of MphR, addition of erythromycin results in proportionally higher reaction rates within a certain dynamic range (FIG. 10).

Example 4—Structure Switching-Based Aptasensor

Figure 11A:
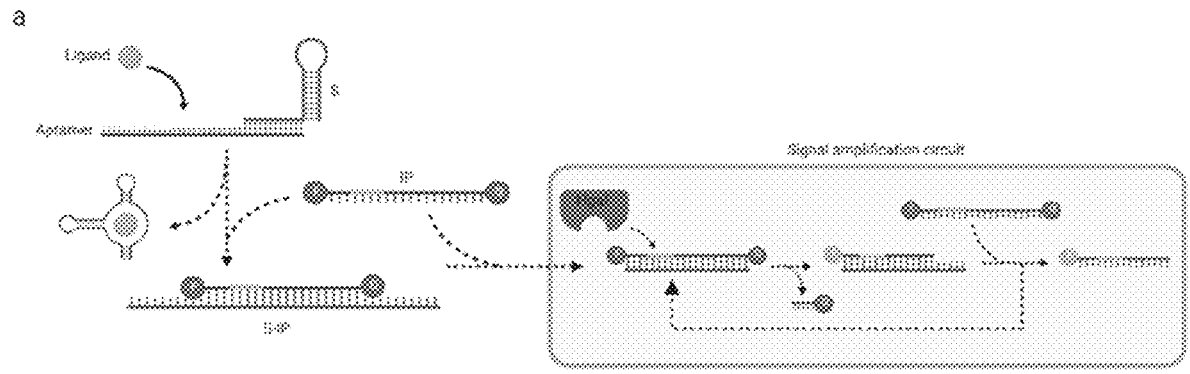
FIGS. 11A-11B are illustrations showing that the endonuclease-mediated toehold-mediated strand displacement (TMSD) circuit can be used to transduce and amplify signals in an aptasensor.
Figure 11B:
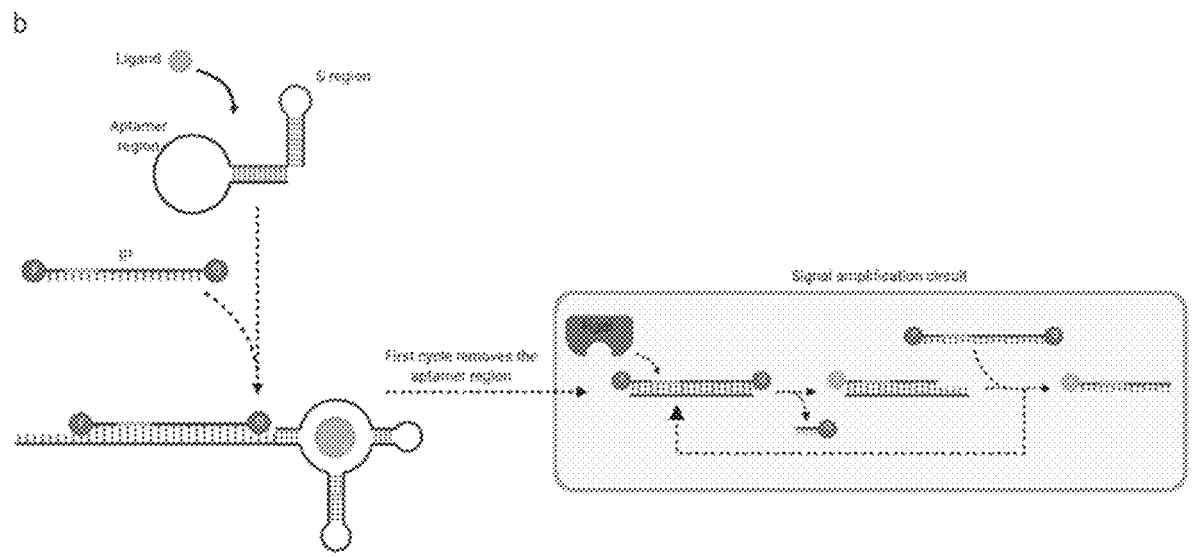

Our circuit can be integrated into an aptasensor by using structure-switching mechanisms in different formats. FIG. 11A shows a scheme utilizing a DNA template (S) with a hairpin structure that contains: 1) the HgaI recognition sequence in the loop region and 2) a single-stranded domain complementary to a ligand-responsive aptamer. The biosensor consists of the template S hybridized to the Aptamer, a labelled probe (modified with fluorophore/quencher pair on the 5' and 3' ends, respectively), and the type IIS restriction enzyme, which can be, but not restricted to, HgaI. The function of the aptamer is dual: 1) inhibit the DNA template from hybridizing to the IP, and 2) bind with high specificity to its ligand. In the presence of the ligand, the aptamer will dissociate from S and IP can hybridize to it, disrupting the hairpin and forming a double stranded product (S-IP). HgaI can then bind and cleave and the TMSD reactions can proceed as previously described. Similarly, FIG. 11B shows a biosensor built using an aptamer switch, where the hairpin structure that contains the HgaI recognition site is located downstream of the aptamer sequence. The single-stranded domain of S is complementary to a region of the aptamer. Similarly, the presence of the ligand in the system causes the dissociation of the double-stranded region between the S and Aptamer regions and IP can bind to S. Once the double-stranded HgaI recognition site is formed, HgaI cleaves off the aptamer/ligand complex generating a toehold domain. Then, the circuit can proceed as previously described.

Figure 12A:
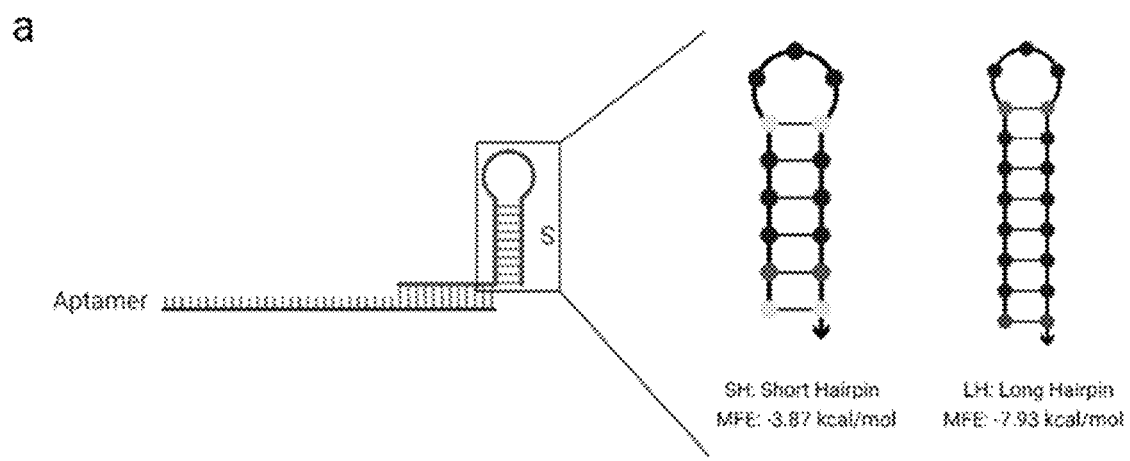
FIGS. 12A-12B show demonstrations that the signal amplification circuit can be triggered by a conformation change on the DNA template S.
Figure 12B:
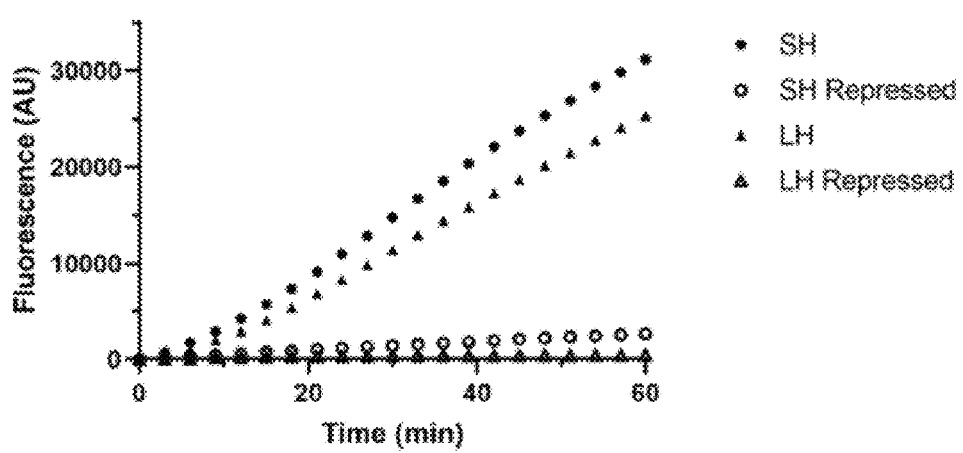

The stability of the hairpin's stem in the DNA template S and the S region in an aptamer switch has a direct effect on the reaction leakage, reaction rate and final concentration of cleaved product. The stability can be varied by changing the length of the stem, which has a direct effect on the minimum free energy of the DNA template (FIG. 12A). In a system with the template S, Aptamer, IP and HgaI (in adequate reaction conditions), the template S with a short hairpin (SH) has higher leakage than a long hairpin (LH) when hybridized to an aptamer strand by 12 base pairs. Also, when the aptamer is not present, hence the reaction is unrepressed, the system with LH is slower than that with SH (FIG. 12B).

Example 5—Signal Amplification with a Lateral Flow Assay Format

Figure 13:
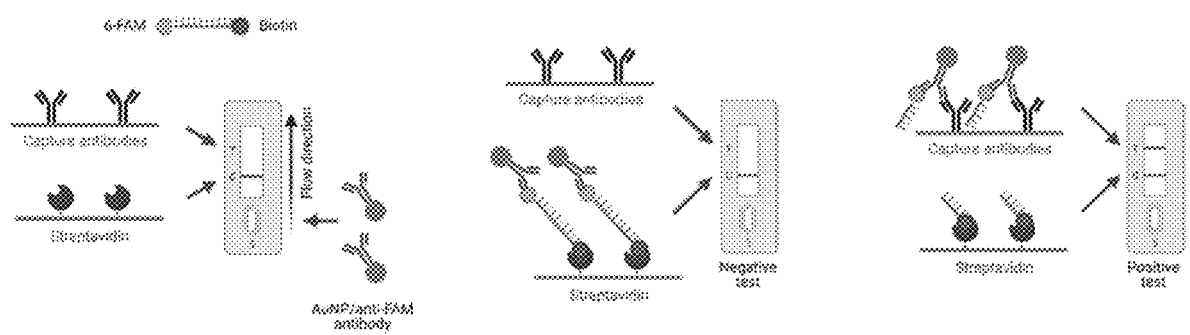
FIG. 13 shows an illustration of the Lateral Flow Assay format. The panel on the left shows the component of the test strip and the modifications of the Invading Probe. The middle panel shows the simplified schematic of a negative test. The right-hand side shows the simplified schematic of a positive test.

Besides fluorescent-based detection, other formats can be used for signal readout. In this example, the IP is modified with different chemical labels at the 5' and 3' than in the fluorescent-based detection. These modifications could be, but are not limited to, 6-FAM, biotin, digoxin, among many others. The biosensor mechanism could be any of the explained above. The difference relies on that the cleaved and displaced DNA product cannot be detected by real-time fluorescence measurements. Instead, after a certain reaction time, the solution is added onto the sample pad of a lateral-flow strip test. FIG. 13 shows an example of a probe modified with 6-FAM and biotin at the 5' and 3' ends, respectively. The lateral flow strip contains gold nanoparticles (AuNPs) functionalized with anti-FAM antibodies on the sample pad (S), immobilized streptavidin on the control region (C) and immobilized capture antibodies on the test region (T). After the reaction, the solution is added onto the sample pad of the paper strip and let flow across its different sections. In a negative test, the 6-FAM label of the uncleaved probe binds to the anti-FAM-functionalized AuNPs and the biotin molecule gets captured by the immobilized streptavidin at the C region, which causes the aggregation of the AuNPs and the C band is shown. This inhibits the probe from flowing any further. Conversely, in a positive test, only the probe fragment that contains the 6-FAM label can bind to the AuNPs through the anti-FAM antibody, while the probe fragment that contains only the biotin label cannot. The latter will be captured in the C region by the immobilized streptavidin and a band will become apparent due to AuNPs aggregation. However, the former will continue flowing until it is captured by the capture antibody in the T region. Thus, a band will become apparent in the T region due to the aggregation of AuNPs. It is to note that this format can be designed to show a test band when the target analyte is present or absent, depending on the configuration of the strip. As well, depending on the strip, the test and control bands can be viewed under the visible spectrum or specific wavelength ranges (e.g. UV).

Example 6—Signal Amplification with an Electrochemical Readout

Figure 14:
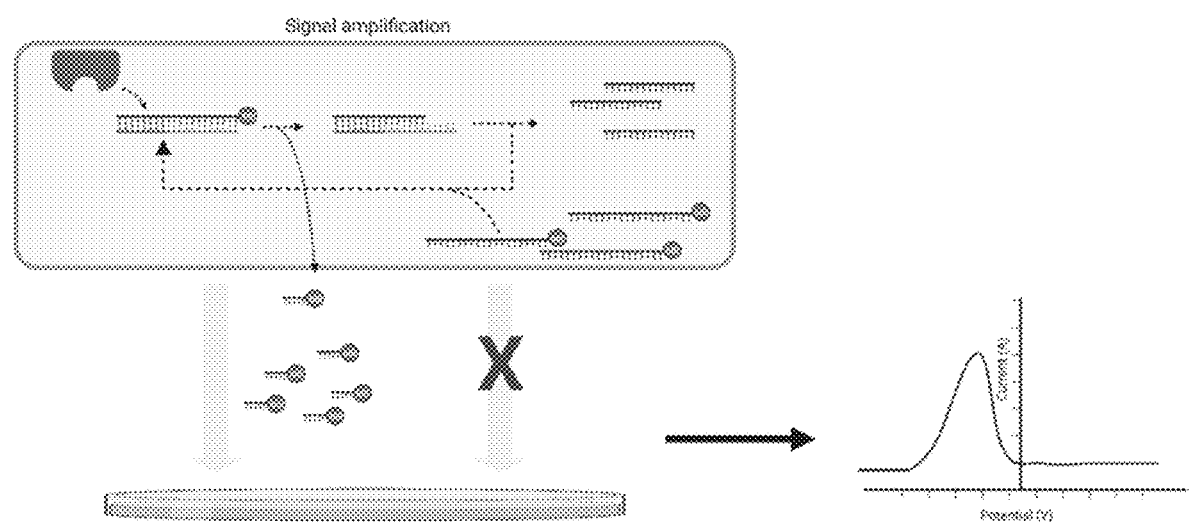
FIG. 14 shows an illustration of the signal amplification circuit with an electrochemical readout.

This example shows that the biosensor circuit signal can be detected through electrochemical methods (FIG. 14). The IP is labeled with an electroactive reporter (e.g. methylene blue), instead of a fluorophore/quencher pair, while keeping the biosensor mechanism the same as described above. After induction of the reaction by the ligand, the cleaved product released is a single-stranded 5-nucleotide long DNA fragment with the electroactive reporter. This short fragment is of less negative charge and molecular weight compared to the full IP and can diffuse more easily to the surface of a carbon screen-printed electrode and generate a change in the current that can be measured using a potentiometer.

Materials and Methods

Strain and Growth Medium. *E. coli* BL21 DE3 (Sangon, China) was used for recombinant protein expression. The growth media used was Lysogeny (LB) agar or broth supplemented with kanamycin (Thermo Fisher Scientific 017924, Waltham, MA) (50 ug/mL).

Plasmid and DNA Parts. pET-28a plasmids encoding aTFs were ordered directly from Sangon Biotech (Shanghai, China). They were designed to express the proteins with a C-terminus His-tag (Table 3). In Table 3, the HgaI recognition site is underlined; the spacer sequence between HgaI binding site and operator sequence is in lower case; the operator sequences are highlighted in bold; FAM is 6-Carboxyfluorescein; and BHQ is Black Hole Quencher. DNA oligonucleotides to form the dsDNA sensor and DNA fluorescent probes (5'6-FAM-3'BHQ1) were ordered from Integrated DNA Technologies (Coralville, IA) (Table 3). The complementary oligonucleotides were annealed in TrisEDTA (TE) buffer pH 7.5, 12.5 mM $MgCl_2$ with a final concentration of 10 μM of dsDNA using a thermocycler (95° C. 5 min, −0.5° C./min, 20° C. 10 min). Dilutions to final working concentrations were made accordingly with TE buffer pH 7.5.

TABLE 3

| Name | |
|---|---|
| TetR<br>SEQ ID NO: 21 | MSRLDKSKVINSALELLNEVGIEGLTTRKLAQKLGVEQPTLYWHVKNKRALLD<br>ALAIEMLDRHHTHFCPLEGESWQDFLRNNAKSFRCALLSHRDGAKVHLGTRPT<br>EKQYETLENQLAFLCQQGFSLENALYALSAVGHFTLGCVLEDQEHQVAKEERE<br>TPTTDSMPPLLRQAIELFDHQGAEPAFLFGLELIICGLEKQLKCESGS |

TABLE 3-continued

Figure 15:
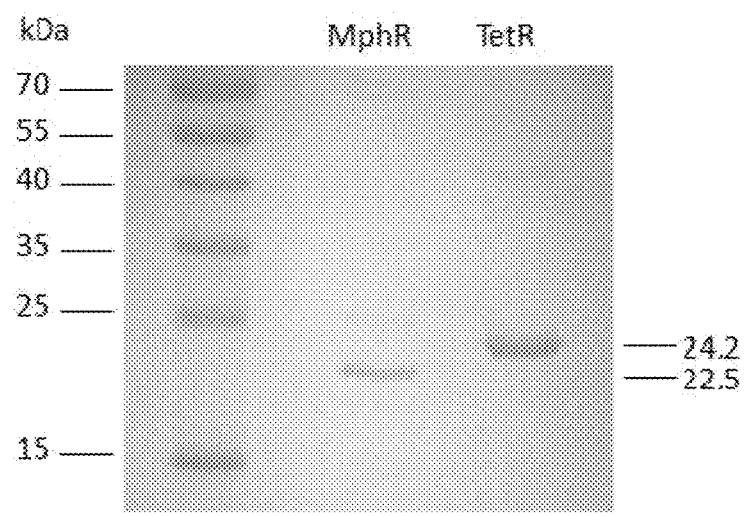
FIG. 15 shows SDS-PAGE of purified TetR and MphR in reducing conditions.

| Name | Sequence |
|---|---|
| MphR<br>SEQ ID NO: 22 | MPRPKLKSDDEVLEAATVVLKRCGPIEFTLSGVAKEVGLSRAALIQRFTNRDT<br>LLVRMMERGVEQVRHYLNAIPIGAGPQGLWEFLQVLVRSMNTRNDFSVNYLIS<br>WYELQVPELRTLAIQRNRAVVEGIRKRLPPGAPAAAELLLHSVIAGATMQWAV<br>DPDGELADHVLAQIAAILCLMFPEHDDFQLLQAHA |
| S_Tc<br>SEQ ID NO: 2 | ATAAAGACGCTCCCTATCAGTGATAGAGA |
| S_Tc'<br>SEQ ID NO: 3 | TCTCTATCACTGATAGGGAGCGTCTTTAT |
| S_Tc +2<br>SEQ ID NO: 5 | ATAAAGACGCagTCCCTATCAGTGATAGAGA |
| S_Tc +2'<br>SEQ ID NO: 6 | TCTCTATCACTGATAGGGActGCGTCTTTAT |
| S_Tc +4<br>SEQ ID NO: 7 | ATAAAGACGCagtcTCCCTATCAGTGATAGAGA |
| S_Tc +4'<br>SEQ ID NO: 8 | TCTCTATCACTGATAGGGAgactGCGTCTTTAT |
| S_Tc +6<br>SEQ ID NO: 9 | ATAAAGACGCagtcagTCCCTATCAGTGATAGAGA |
| S_Tc +6'<br>SEQ ID NO: 10 | TCTCTATCACTGATAGGGActgactGCGTCTTTAT |
| S_Tc +8<br>SEQ ID NO: 11 | ATAAAGACGCagtcagtcTCCCTATCAGTGATAGAGA |
| S_Tc +8'<br>SEQ ID NO: 12 | TCTCTATCACTGATAGGGAgactgactGCGTCTTTAT |
| S_Tc +10<br>SEQ ID NO: 13 | ATAAAGACGCagtcagtcagTCCCTATCAGTGATAGAGA |
| S_Tc +10'<br>SEQ ID NO: 14 | TCTCTATCACTGATAGGGActgactgactGCGTCTTTAT |
| S_Tc +12<br>SEQ ID NO: 15 | ATAAAGACGCagtcagtcagtcTCCCTATCAGTGATAGAGA |
| S_Tc +12'<br>SEQ ID NO: 16 | TCTCTATCACTGATAGGGAgactgactgactGCGTCTTTAT |
| S_Ery<br>SEQ ID NO: 17 | ATAAAGACGCGAATATAACCGACGTGACTGTTACATTTAGGTGG |
| S_Ery'<br>SEQ ID NO: 18 | CCACCTAAATGTAACAGTCACGTCGGTTATATTCGCGTCTTTAT |
| IP_Tc<br>SEQ ID NO: 19 | FAM-ATAAAGACGCTCCCTATCAGTGA-BHQ |
| IP_Ery<br>SEQ ID NO: 20 | FAM-ATAAAGACGCGAATATAACCGAC-BHQ | aTF Expression and Purification. Streak-plating onto LB Agar supplemented with kanamycin was used to pick single colonies of E. coli BL21 DE3 containing pET-28a. A single colony was used to grow a 10 mL overnight culture at 200 rpm and 37° C. and subsequently a 500 mL culture. At OD600 of 0.5, the culture was induced with 250 μM IPTG (Sigma-Aldrich #I6758, St. Louis, MO) and grown for 5 h in the 200 rpm and 37° C. The cell pellet was recovered after centrifugation at 3,300×g for 20 min and resuspended in lysis buffer (PBS pH 7.4 (Thermo Fisher Scientific #28372), 1× Halt Protease Inhibitor (Thermo Fisher Scientific #1861278), 10 mM Imidazole) or kept at −20° C. for a maximum of 7 days in PBS pH 7.4. The suspension was ultrasonicated on ice (5 cycles of 1 min with 1 min of rest, 50% duty cycle) and centrifuged at 13,000×g for 30 min. The supernatant was then used to purify the His-Tagged proteins using Ni-NTA agarose (Qiagen #30210, Hilden, Germany) in a gravity column (10 mM, 25 mM, and 250 mM imidazole in PBS for equilibration, washing, and elution, respectively). Centrifugal filters (Amicon Ultra 4, Millipore, Burlington, MA) were used to desalt (the final buffer was PBS) and concentrate the purified protein. Confirmation of the purification was carried out by reducing SDS-PAGE 12% (FIG. 15) and concentration determination by Bradford Assay. Proteins were kept at −20° C. in 50% glycerol, and dilutions were made accordingly with PBS.

Figure 5A:
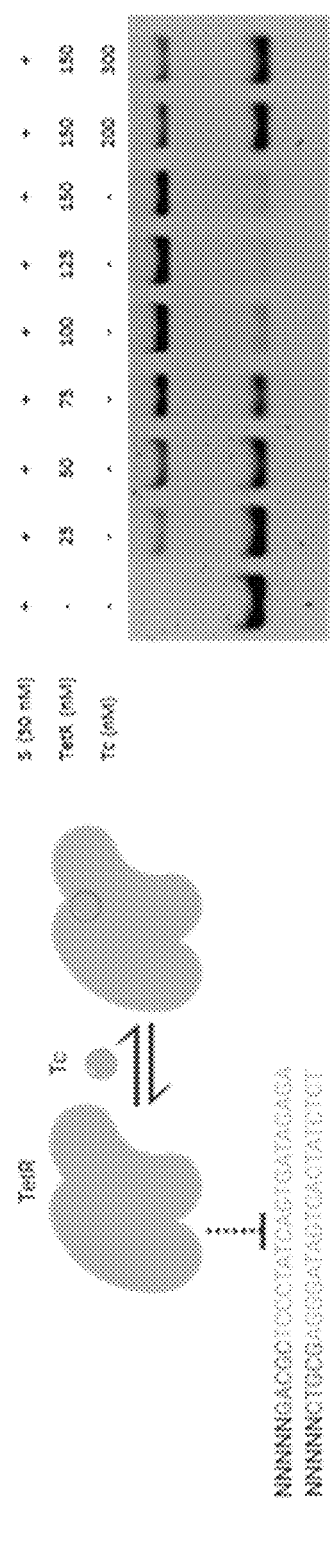
FIGS. 5A-5C show that allostery mediates HgaI cleavage.
Figure 5B:
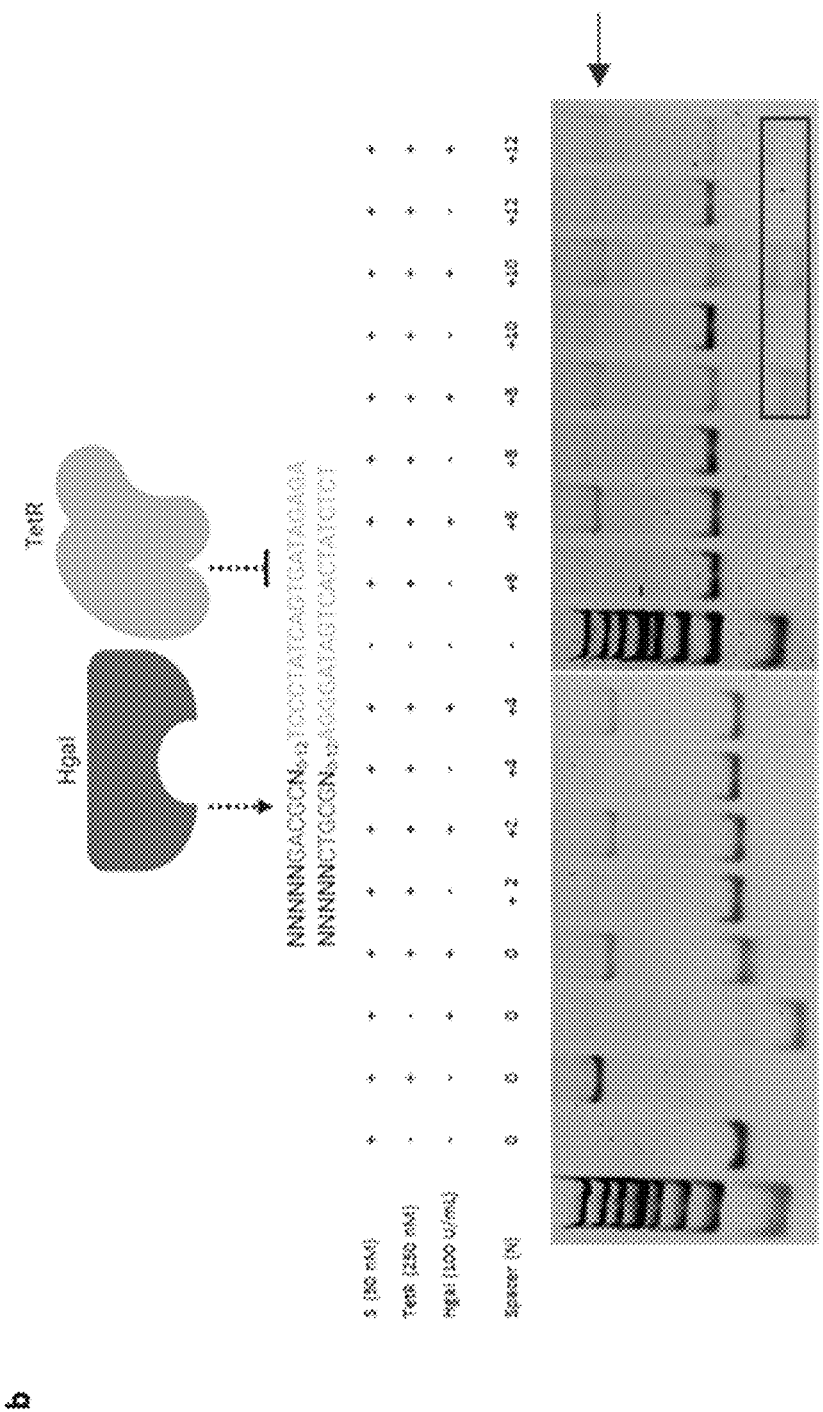

Gel Electrophoresis and Electrophoretic Mobility Shift Assay. PAGE 12% (room temperature at 90 V in TBE 1× buffer) was used to visualize the activity of HgaI on DNA templates with spacers of different length (SEQ ID NOs: 2-16) (FIG. 5B). Reactions containing DNA template, TetR, and HgaI were incubated at 37° C. and stopped after 30 min by the addition of Proteinase K (New England Biolabs #P8107S, Ipswich, MA) and incubation for 10 additional minutes. This step was to stop HgaI and release any non-cleaved DNA from TetR.

Figure 5C:
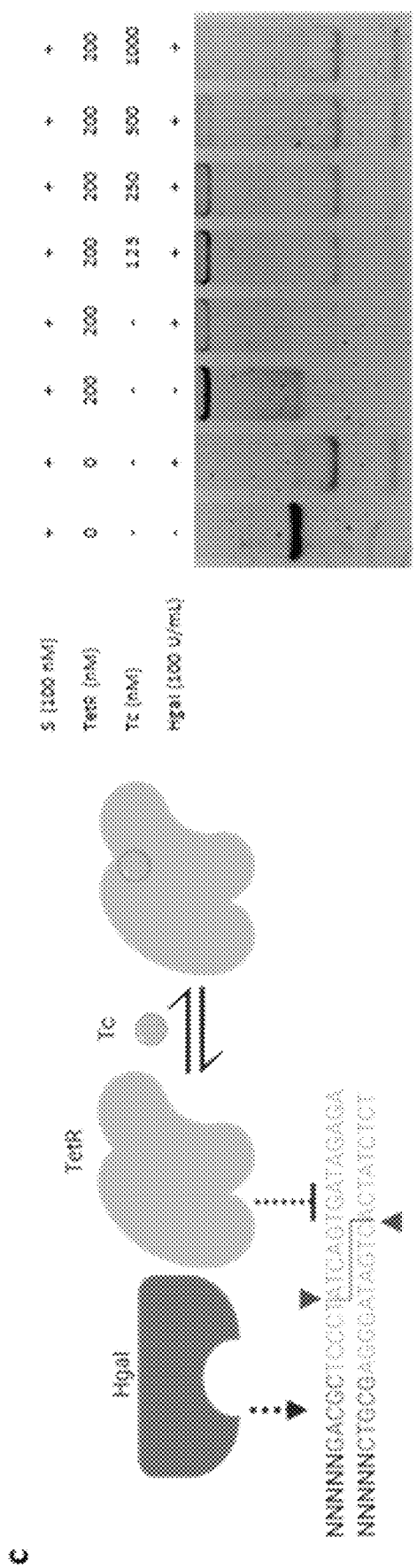

To evaluate the allostery of the TetR (FIG. 5A and FIG. 5C) dsDNA was mixed with the different ratios of the aTF and equilibrated in NEBuffer 1.1 (New England Biolabs #B7201S) at room temperature. EMSA was carried out on PAGE 10% at room temperature at 90 V in TBE 1× buffer. Post staining was done with SYBRGold (Thermo Fisher Scientific #S11494) 1× in TBE 1× buffer.

Reaction compositions are as described in the corresponding figures, and all were performed using a final concentration of 1×NEBuffer 1.1 (New England Biolabs #B7201S), unless indicated otherwise.

HgaI/Toehold-Mediated Strand Displacement Reactions. Reactions were set up by adding Buffer 1.1 (New England Biolabs), dsDNA template, invading probe, aTF, nuclease-free water (Integrated DNA Technologies) or sample, and HgaI (New England Biolabs), to a final volume of 10 uL. Immediately after adding HgaI, 6-FAM fluorescence intensity was monitored over 30-120 min on a CFX96 Touch Real Time PCR Detection System (Bio-Rad Laboratories, Inc., Hercules, CA) on Channel 1. Detailed formulation of HgaI restriction reactions can be found in Table 4.

TABLE 4

| Component | Stock Concentration | Volume (µL) | Final concentration |
|---|---|---|---|
| dsDNA template | 1 µM | 0.5 | 50 nM |
| aTF | Varies | 1.75 | Varies |
| Probe | 10 µM | 1.25 | 1.25 µM |
| Water or sample | — | 5 µL | — |
| Buffer 1.1 NEB | 10X | 1 | 1X |
| Hga1 | 2000 U/mL | 0.5 | 100 U/mL |
| Final | — | 10 µL | — |

Figure 6A:
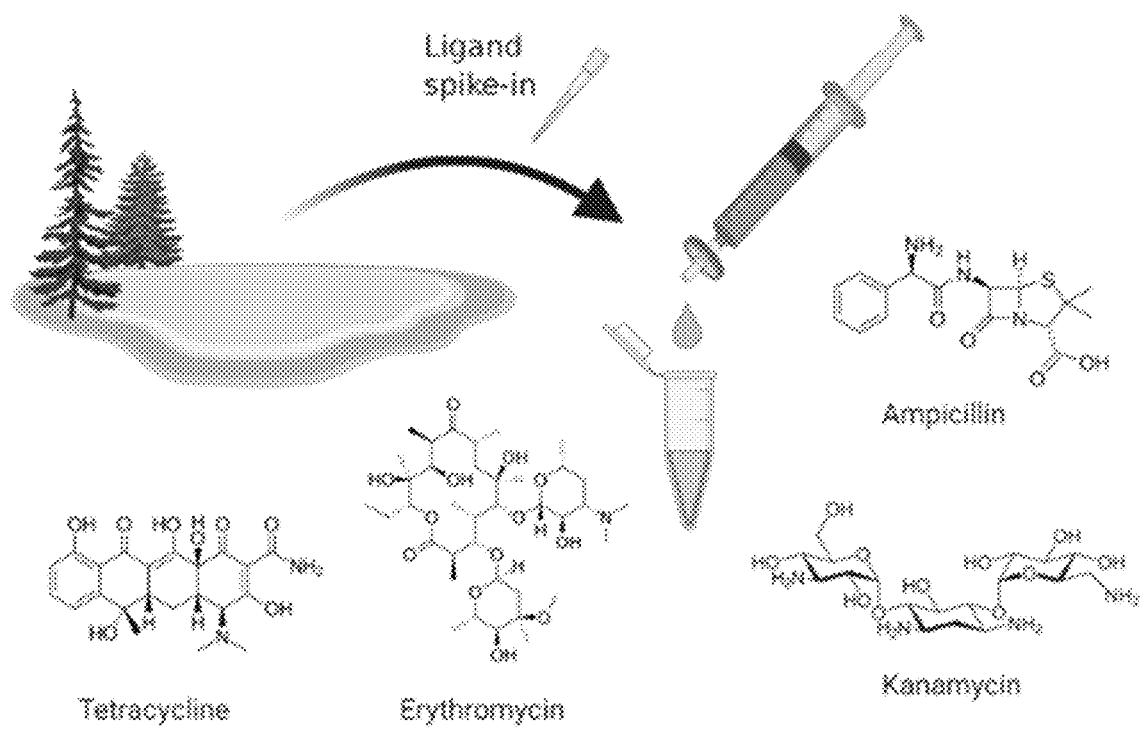
FIGS. 6A-6C show test of the biosensors with environmental matrices.
Figure 6B:
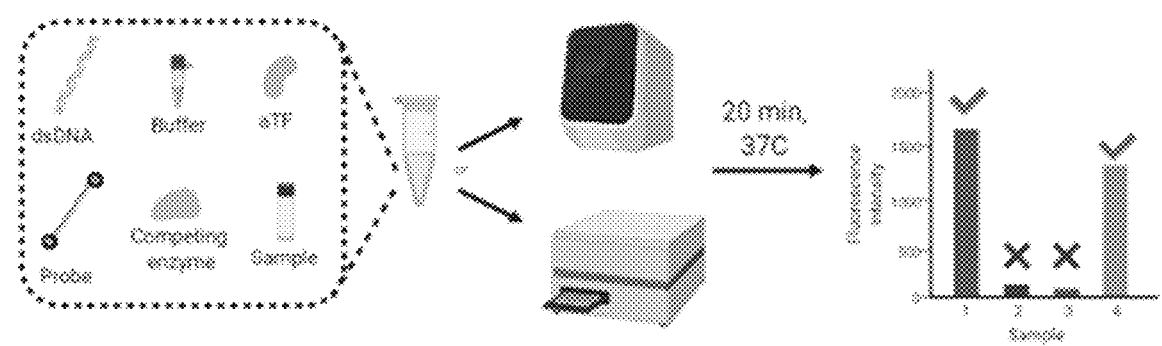
Figure 6C:
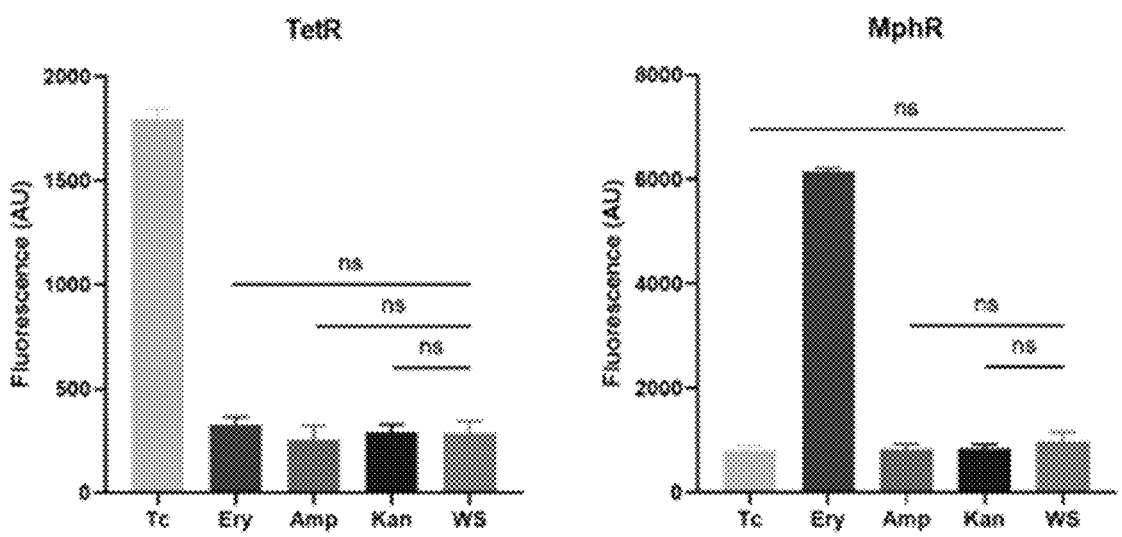

Water Sampling and Processing. Water samples were taken from a pond in eastern Hong Kong (22.332022, 114.245774). Samples were collected in sterile 50 mL Falcon tubes and transported to the lab at room temperature (1 h). In the lab, they were filtered using a 0.45 µm syringe filter and immediately used for the reactions. Corresponding samples were spiked with known concentrations of tetracycline (see SigmaACS Synthetic Biology pubs.acs.org/synthbio Research Article https://dx.doi.org/10.1021/acssynbio.0c00545 ACS Synth. Biol. 2021, 10, 371-378 376 Sigma-Aldrich #87128), erythromycin (Sangon Biotech CAS #114-07-8), kanamycin (Thermo Fisher Scientific 017924), or ampicillin (Sigma-Aldrich #A9518) prior to filtering. All reactions using water samples (spiked or not) were performed on the day of collection, with a maximum of 2 h between collection and reaction. For data shown in FIG. 6C 500 nM (final concentration 250 nM) antibiotics was used to test the TetR-based biosensor, and 2.5 µM (final concentration 1.25 nM) was used with the MphR-based biosensor. 50 nM of DNA template and 1.25 µM of Invading Probe were used in all reactions (FIGS. 6A-6C).

Data Processing and Visualization. All raw data was processed and analyzed with Microsoft Excel and GraphPad Prism 8. All graphs were generated with GraphPad 8(Prism, San Diego, CA) and Matlab (Mathworks, Portola Valley, CA). Schemes and illustrations were created with Biorender.com.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES (2) Vanarsdale, E.; Tsao, C. Y.; Liu, Y.; Chen, C. Y.; Payne, G. F.; Bentley, W. E. Redox-Based Synthetic Biology Enables Electrochemical Detection of the Herbicides Dicamba and Roundup via Rewired *Escherichia coli*. ACS Sensors 2019, 4, 1180-1184. https://doi.org/10.1021/acssensors.9b00085.

(3) Wen, K. Y.; Cameron, L.; Chappell, J.; Jensen, K.; Bell, D. J.; Kelwick, R.; Kopniczky, M.; Davies, J. C.; Filloux, A.; Freemont, P. S. A Cell-Free Biosensor for Detecting Quorum Sensing Molecules in *P. aeruginosa*-Infected Respiratory Samples. ACS Synth. Biol. 2017, 6, 2293-2301. https://doi.org/10.1021/acssynbio.7b00219.

(4) Dietrich, J.; Keasling, J. Transcription Factor-Based Biosensors for Detecting Dicarboxylic Acids. U.S. Pat. No. 8,652,804B2, Feb. 18, 2014.

(5) Mandell, D. J.; Feng, J.; Villanueva, X. R.; Chari, R. Small Molecule Biosensors. WO/2017/048316A1, Sep. 13, 2018.

(6) Silverman, A. D.; Akova, U.; Alam, K. K.; Jewett, M. C.; Lucks, J. B. Design and Optimization of a Cell-Free Atrazine Biosensor. ACS Synth. Biol. 2020, 9, 671-677. https://doi.org/10.1021/acssynbio.9b00388.

(7) Jewett, M. C.; Lucks, J. B.; Silverman, A. D.; Alam, K. K. On Demand, Portable, Cell-Free Molecular Sensing Platform. WO/2020/072127, Apr. 9, 2020.

(8) Cao, J.; Yao, Y.; Fan, K.; Tan, G.; Xiang, W.; Xia, X.; Li, S.; Wang, W.; Zhang, L. Harnessing a Previously Unidentified Capability of Bacterial Allosteric Transcription Factors for Sensing Diverse Small Molecules in Vitro. Sci. Adv. 2018, 4, eaau4602. https://doi.org/10.1126/sciadv.aau4602.

(9) Yao, Y.; Li, S.; Cao, J.; Liu, W.; Fan, K.; Xiang, W.; Yang, K.; Kong, D.; Wang, W. Development of Small Molecule Biosensors by Coupling the Recognition of the Bacterial Allosteric Transcription Factor with Isothermal Strand Displacement Amplification. Chem. Commun. 2018, 54, 4774-4777. https://doi.org/10.1039/c8cc01764f.

(10) Yao, Y.; Li, S.; Cao, J.; Liu, W.; Qi, F.; Xiang, W.; Yang, K.; Wang, W.; Zhang, L. A Novel Signal Transduction System for Development of Uric Acid Biosensors. Appl. Microbiol. Biotechnol. 2018, 102, 7489-7497. https://doi.org/10.1007/s00253-018-9056-8.

(11) Liang, M.; Li, Z.; Wang, W.; Liu, J.; Liu, L.; Zhu, G.; Karthik, L.; Wang, M.; Wang, K. F.; Wang, Z.; et al. A CRISPR-Cas12a-Derived Biosensing Platform for the Highly Sensitive Detection of Diverse Small Molecules. Nat. Commun. 2019, 10. https://doi.org/10.1038/s41467-019-11648-1.

We claim:

1. A method of detecting an analyte in a sample of regulating DNA circuits, the method comprising:
   a) contacting the sample to a composition comprising a restriction enzyme, a DNA template, a sensor molecule, and an invading probe, wherein the analyte binds to the sensor molecule and permits recognition of a restriction site in the DNA template by the restriction enzyme and wherein the invading probe generates a detectable signal in conjunction with a reporter molecule and
   b) binding the sensor molecule to the DNA template; wherein the sensor molecule excludes the restriction enzyme from a restriction site specific to said restriction enzyme in the DNA template in the absence of the analyte or displacing the sensor molecule from the DNA template if the analyte is present and binds to the sensor molecule,
   wherein the sensor molecule is an allosteric transcription factor or an aptamer,
   wherein the analyte is a ligand that binds to the sensor molecule,
   wherein the restriction enzyme is a type IIS restriction enzyme that generates an overhang at the 3' end or 5' end of the DNA template and the overhang is at least four nucleotides in length,
   wherein the DNA template is a double-stranded DNA sequence that contains at least one restriction site upstream or downstream of at least one operator sequence or a single-stranded DNA sequence that contains restriction site in the loop region of a hairpin structure and a domain complementary to an aptamer molecule, and wherein the invading probe is a single-stranded DNA sequence that is partially or fully complementary to the DNA template.

2. The method of claim 1, wherein if the analyte is present, the method further comprises:
c) digesting the DNA template with the restriction enzyme;
d) hybridizing the invading probe to the DNA template;
e) cleaving the hybridized invading probe and DNA template with the restriction enzyme; and
f) determining the presence or absence of at least one analyte by detecting a signal emitted from the cleaved hybridized invading probe and DNA template, wherein detection of said signal is indicative of the presence of the analyte.

3. The method of claim 1, wherein the analyte is selected from antibiotics, aromatic compounds, quorum sensing molecules, or metals.

4. The method of claim 1, wherein the signal is an electrochemical, fluorescent, luminescent, and/or colorimetric signal.

5. The method of claim 1, further comprising contacting the sample to a buffer suitable for a restriction enzyme cleavage reaction and toehold-mediated strand displacement reaction.

6. The method of claim 1, wherein the sample is treated prior to step a) by heating, centrifugation, chemical or physical solubilization, dilution, concentration, or filtration.

7. The method of claim 1, wherein step a) and step b) are performed at a temperature of about 20° C. to about 60° C.

8. The method of claim 2, wherein step c), step d), and step e) are performed at a temperature of about 20° C. to about 60° C.

9. The method of claim 2, wherein step e) further comprises hybridizing the invading probe to a toehold domain in the cleaved hybridized invading probe and DNA template and displacing a short strand of the cleaved DNA fragment by the invading probe; and repeating steps d) and e) until the restriction enzyme is deactivated, there is no remaining uncleaved invading probe, or the restriction site specific to said restriction enzyme is blocked.

* * * * *

SEQUENCE LISTING

<160> NUMBER OF SEQ ID NOS: 22

<210> SEQ ID NO 1
<211> LENGTH: 642
<212> TYPE: DNA
<213> ORGANISM: Escherichia coli

<400> SEQUENCE: 1

```
atgagtcggt tagacaagag taaagtgatt aattcggctc tcgaactgct gaatgaagtt      60
gggattgagg ggttgactac ccgcaaatta gcacagaaac ttggcgtaga acagccaact     120
ctttactggc acgttaagaa taagcgggcc cttcttgatg cgcttgccat cgagatgctg     180
```

```
gaccgccatc acacacactt tgcccatta gaaggggagt cgtggcagga tttcttacgg      240
aataatgcca agtctttccg gtgcgctctt cttagccatc gtgacggtgc aaaggtacat      300
ttaggcacgc gcccgaccga aaaacagtac gaaaccttag aaaaccagct tgcctttctg      360
tgtcaacagg gtttcagcct cgaaaatgcg ttatacgctc tgtcggccgt aggccacttt      420
acgctcgggt gcgtcctcga ggaccaagag caccaggtcg ctaaggagga gcgggagacc      480
ccaaccacag atagtatgcc accattgtta cgtcaagcaa tcgagttgtt tgatcaccaa      540
ggtgcggagc ctgcatttct ttttggttta gaactgatta tctgtggcct tgaaaagcag      600
ttgaaatgcg aaagcgggtc ctgacatcat catcatcatc at                         642
```

<210> SEQ ID NO 2
<211> LENGTH: 29
<212> TYPE: DNA
<213> ORGANISM: Artificial Sequence
<220> FEATURE:
<223> OTHER INFORMATION: DNA template sequence for use with TetR sensor
      molecule

<400> SEQUENCE: 2

```
ataaagacgc tccctatcag tgatagaga                                         29
```

<210> SEQ ID NO 3
<211> LENGTH: 29
<212> TYPE: DNA
<213> ORGANISM: Artificial Sequence
<220> FEATURE:
<223> OTHER INFORMATION: DNA template sequence for use with TetR sensor
      molecule

<400> SEQUENCE: 3

```
tctctatcac tgatagggag cgtctttat                                         29
```

<210> SEQ ID NO 4
<211> LENGTH: 23
<212> TYPE: DNA
<213> ORGANISM: Artificial Sequence
<220> FEATURE:
<223> OTHER INFORMATION: exemplary invading probe
<220> FEATURE:
<221> NAME/KEY: misc_feature
<222> LOCATION: (1)..(1)
<223> OTHER INFORMATION: FAM
<220> FEATURE:
<221> NAME/KEY: misc_feature
<222> LOCATION: (23)..(23)
<223> OTHER INFORMATION: BHQ

<400> SEQUENCE: 4

```
ataaagacgc tccctatcag tga                                               23
```

<210> SEQ ID NO 5
<211> LENGTH: 31
<212> TYPE: DNA
<213> ORGANISM: Artificial Sequence
<220> FEATURE:
<223> OTHER INFORMATION: DNA template sequence for use with TetR sensor
      molecule

<400> SEQUENCE: 5

```
ataaagacgc agtccctatc agtgatagag a                                      31
```

<210> SEQ ID NO 6
<211> LENGTH: 31

<212> TYPE: DNA
<213> ORGANISM: Artificial Sequence
<220> FEATURE:
<223> OTHER INFORMATION: DNA template sequence for use with TetR sensor
      molecule

<400> SEQUENCE: 6
tctctatcac tgatagggac tgcgtctttt a                                    31

<210> SEQ ID NO 7
<211> LENGTH: 33
<212> TYPE: DNA
<213> ORGANISM: Artificial Sequence
<220> FEATURE:
<223> OTHER INFORMATION: DNA template sequence for use with TetR sensor
      molecule

<400> SEQUENCE: 7
ataaagacgc agtctcccta tcagtgatag aga                                  33

<210> SEQ ID NO 8
<211> LENGTH: 33
<212> TYPE: DNA
<213> ORGANISM: Artificial Sequence
<220> FEATURE:
<223> OTHER INFORMATION: DNA template sequence for use with TetR sensor
      molecule

<400> SEQUENCE: 8
tctctatcac tgatagggag actgcgtctt tat                                  33

<210> SEQ ID NO 9
<211> LENGTH: 35
<212> TYPE: DNA
<213> ORGANISM: Artificial Sequence
<220> FEATURE:
<223> OTHER INFORMATION: DNA template sequence for use with TetR sensor
      molecule

<400> SEQUENCE: 9
ataaagacgc agtcagtccc tatcagtgat agaga                                35

<210> SEQ ID NO 10
<211> LENGTH: 35
<212> TYPE: DNA
<213> ORGANISM: Artificial Sequence
<220> FEATURE:
<223> OTHER INFORMATION: DNA template sequence for use with TetR sensor
      molecule

<400> SEQUENCE: 10
tctctatcac tgatagggac tgactgcgtc tttat                                35

<210> SEQ ID NO 11
<211> LENGTH: 37
<212> TYPE: DNA
<213> ORGANISM: Artificial Sequence
<220> FEATURE:
<223> OTHER INFORMATION: DNA template sequence for use with TetR sensor
      molecule

<400> SEQUENCE: 11
ataaagacgc agtcagtctc cctatcagtg atagaga                              37

<210> SEQ ID NO 12
<211> LENGTH: 37
<212> TYPE: DNA

<213> ORGANISM: Artificial Sequence
<220> FEATURE:
<223> OTHER INFORMATION: DNA template sequence for use with TetR sensor
      molecule

<400> SEQUENCE: 12
tctctatcac tgatagggag actgactgcg tctttat                                37

<210> SEQ ID NO 13
<211> LENGTH: 39
<212> TYPE: DNA
<213> ORGANISM: Artificial Sequence
<220> FEATURE:
<223> OTHER INFORMATION: DNA template sequence for use with TetR sensor
      molecule

<400> SEQUENCE: 13
ataaagacgc agtcagtcag tccctatcag tgatagaga                              39

<210> SEQ ID NO 14
<211> LENGTH: 39
<212> TYPE: DNA
<213> ORGANISM: Artificial Sequence
<220> FEATURE:
<223> OTHER INFORMATION: DNA template sequence for use with TetR sensor
      molecule

<400> SEQUENCE: 14
tctctatcac tgatagggac tgactgactg cgtctttat                              39

<210> SEQ ID NO 15
<211> LENGTH: 41
<212> TYPE: DNA
<213> ORGANISM: Artificial Sequence
<220> FEATURE:
<223> OTHER INFORMATION: DNA template sequence for use with TetR sensor
      molecule

<400> SEQUENCE: 15
ataaagacgc agtcagtcag tctccctatc agtgatagag a                           41

<210> SEQ ID NO 16
<211> LENGTH: 41
<212> TYPE: DNA
<213> ORGANISM: Artificial Sequence
<220> FEATURE:
<223> OTHER INFORMATION: DNA template sequence for use with TetR sensor
      molecule

<400> SEQUENCE: 16
tctctatcac tgatagggag actgactgac tgcgtcttta t                           41

<210> SEQ ID NO 17
<211> LENGTH: 44
<212> TYPE: DNA
<213> ORGANISM: Artificial Sequence
<220> FEATURE:
<223> OTHER INFORMATION: DNA template sequence for use with MphR sensor
      molecule

<400> SEQUENCE: 17
ataaagacgc gaatataacc gacgtgactg ttacatttag gtgg                        44

<210> SEQ ID NO 18
<211> LENGTH: 44
<212> TYPE: DNA
<213> ORGANISM: Artificial Sequence

```
<220> FEATURE:
<223> OTHER INFORMATION: DNA template sequence for use with MphR sensor
      molecule

<400> SEQUENCE: 18
ccacctaaat gtaacagtca cgtcggttat attcgcgtct ttat            44

<210> SEQ ID NO 19
<211> LENGTH: 23
<212> TYPE: DNA
<213> ORGANISM: Artificial Sequence
<220> FEATURE:
<223> OTHER INFORMATION: exemplary invading probe
<220> FEATURE:
<221> NAME/KEY: misc_feature
<222> LOCATION: (1)..(1)
<223> OTHER INFORMATION: FAM
<220> FEATURE:
<221> NAME/KEY: misc_feature
<222> LOCATION: (23)..(23)
<223> OTHER INFORMATION: BHQ

<400> SEQUENCE: 19
ataaagacgc tccctatcag tga                                   23

<210> SEQ ID NO 20
<211> LENGTH: 23
<212> TYPE: DNA
<213> ORGANISM: Artificial Sequence
<220> FEATURE:
<223> OTHER INFORMATION: exemplary invading probe
<220> FEATURE:
<221> NAME/KEY: misc_feature
<222> LOCATION: (1)..(1)
<223> OTHER INFORMATION: FAM
<220> FEATURE:
<221> NAME/KEY: misc_feature
<222> LOCATION: (23)..(23)
<223> OTHER INFORMATION: BHQ

<400> SEQUENCE: 20
ataaagacgc gaatataacc gac                                   23

<210> SEQ ID NO 21
<211> LENGTH: 207
<212> TYPE: PRT
<213> ORGANISM: Escherichia coli

<400> SEQUENCE: 21

Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
    50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125
```

```
Asn Ala Leu Tyr Ala Leu Ser Ala Val Gly His Phe Thr Leu Gly Cys
            130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser
            195                 200                 205

<210> SEQ ID NO 22
<211> LENGTH: 194
<212> TYPE: PRT
<213> ORGANISM: Escherichia coli

<400> SEQUENCE: 22

Met Pro Arg Pro Lys Leu Lys Ser Asp Asp Glu Val Leu Glu Ala Ala
1               5                   10                  15

Thr Val Val Leu Lys Arg Cys Gly Pro Ile Glu Phe Thr Leu Ser Gly
            20                  25                  30

Val Ala Lys Glu Val Gly Leu Ser Arg Ala Ala Leu Ile Gln Arg Phe
            35                  40                  45

Thr Asn Arg Asp Thr Leu Leu Val Arg Met Met Glu Arg Gly Val Glu
        50                  55                  60

Gln Val Arg His Tyr Leu Asn Ala Ile Pro Ile Gly Ala Gly Pro Gln
65              70                  75                  80

Gly Leu Trp Glu Phe Leu Gln Val Leu Val Arg Ser Met Asn Thr Arg
            85                  90                  95

Asn Asp Phe Ser Val Asn Tyr Leu Ile Ser Trp Tyr Glu Leu Gln Val
            100                 105                 110

Pro Glu Leu Arg Thr Leu Ala Ile Gln Arg Asn Arg Ala Val Val Glu
            115                 120                 125

Gly Ile Arg Lys Arg Leu Pro Pro Gly Ala Pro Ala Ala Ala Glu Leu
130                 135                 140

Leu Leu His Ser Val Ile Ala Gly Ala Thr Met Gln Trp Ala Val Asp
145                 150                 155                 160

Pro Asp Gly Glu Leu Ala Asp His Val Leu Ala Gln Ile Ala Ala Ile
            165                 170                 175

Leu Cys Leu Met Phe Pro Glu His Asp Asp Phe Gln Leu Leu Gln Ala
            180                 185                 190

His Ala
```